(12) United States Patent
Lapham et al.

(10) Patent No.: US 9,643,185 B2
(45) Date of Patent: May 9, 2017

(54) HIGH-THROUGHPUT SAMPLE PROCESSING SYSTEMS AND METHODS OF USE

(71) Applicant: Counsyl, Inc., South San Francisco, CA (US)

(72) Inventors: Kyle Allen Lapham, San Francisco, CA (US); James Frederick Cregg, San Francisco, CA (US); Daniel Delubac, Los Altos, CA (US); Stuart Ira Glaser, San Francisco, CA (US)

(73) Assignee: Counsyl, Inc., South San Francisco, CA (US)

( * ) Notice: Subject to any disclaimer, the term of this patent is extended or adjusted under 35 U.S.C. 154(b) by 0 days.

(21) Appl. No.: 15/095,026

(22) Filed: Apr. 9, 2016

(65) Prior Publication Data

US 2016/0354783 A1 Dec. 8, 2016

Related U.S. Application Data

(63) Continuation of application No. 14/728,017, filed on Jun. 2, 2015, now Pat. No. 9,339,817.

(60) Provisional application No. 62/038,045, filed on Aug. 15, 2014.

(51) Int. Cl.
| | | |
|---|---|---|
| *G01N 1/10* | (2006.01) |
| *B01L 3/00* | (2006.01) |
| *G01N 1/38* | (2006.01) |
| *C12Q 1/68* | (2006.01) |
| *G01N 35/02* | (2006.01) |
| *G01N 35/10* | (2006.01) |
| *B01L 3/02* | (2006.01) |
| *B01L 99/00* | (2010.01) |
| *G01N 35/00* | (2006.01) |
| *B01L 7/00* | (2006.01) |

(52) U.S. Cl.
CPC ............... *B01L 3/527* (2013.01); *B01L 3/021* (2013.01); *B01L 3/5025* (2013.01); *B01L 99/00* (2013.01); *C12Q 1/6806* (2013.01); *G01N 1/38* (2013.01); *G01N 35/00732* (2013.01); *G01N 35/028* (2013.01); *G01N 35/1002* (2013.01); *G01N 35/1016* (2013.01); *G01N 35/1074* (2013.01); *B01L 7/00* (2013.01); *B01L 2200/082* (2013.01); *B01L 2200/143* (2013.01); *B01L 2300/021* (2013.01); *B01L 2300/0627* (2013.01); *B01L 2300/0829* (2013.01); *B01L 2400/0487* (2013.01); *G01N 2035/00356* (2013.01); *G01N 2035/00376* (2013.01); *G01N 2035/00396* (2013.01); *G01N 2035/00752* (2013.01); *G01N 2035/1025* (2013.01); *G01N 2035/1034* (2013.01)

(58) Field of Classification Search
CPC ......................... G01N 33/491; B01L 2200/143
USPC .................................. 436/177, 180; 422/517
See application file for complete search history.

(56) References Cited

U.S. PATENT DOCUMENTS 5,578,270 A * 11/1996 Reichler .................. B01L 3/502
422/510

* cited by examiner

*Primary Examiner* — Natalia Levkovich
(74) *Attorney, Agent, or Firm* — FisherBroyles, LLP; Victoria L. Boyd

(57) ABSTRACT

Disclosed herein are high-throughput sample processing systems and waste management systems, and methods of using the same.

12 Claims, 8 Drawing Sheets

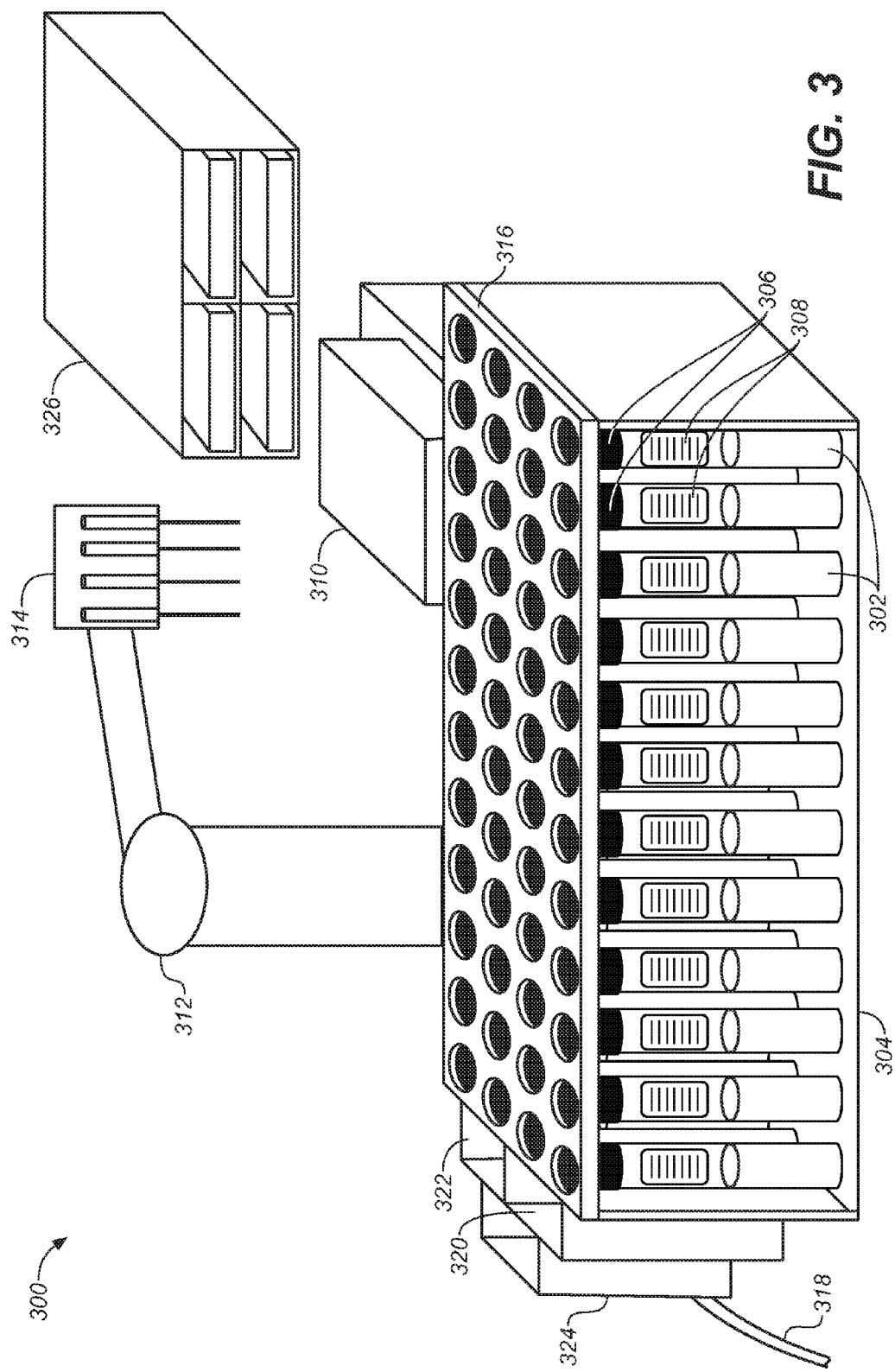

HIGH-THROUGHPUT SAMPLE PROCESSING SYSTEMS AND METHODS OF USE

RELATED APPLICATIONS

This application is a Continuation of U.S. application Ser. No. 14/728,017 filed, now U.S. Pat. No. 9,339,817, which claims priority to U.S. Provisional Application Ser. No. 62/038,045. The disclosures of the foregoing applications are herein incorporated by reference in their entireties.

FIELD OF THE INVENTION

The present invention relates to the field of sample processing. More specifically, the present disclosure relates to high-throughput sample processing systems and waste management systems, and methods of using the same.

BACKGROUND OF THE INVENTION

Research or diagnostic laboratories commonly process biological samples to extract target molecules, such as proteins or DNA, for further research or diagnostic purposes. Consistent sample processing requires time-intensive labor from trained technicians or the use of previously known sample processing systems, which have low sample throughput, result in high costs, and risk worker exposure to hazardous waste.

Previously known sample processing systems are limited in the number of samples that can be simultaneously processed, provide limited versatility for extracting different types of target molecules or for integrating different processing steps, and generate substantial amounts of solid and liquid waste. For example, these previous automated processing systems are often capable of processing a single sample processing plate at a time. Furthermore, these systems require a technician to remove a processed sample processing plate and insert a new sample processing plate for processing after each completed process. Additionally, previously known automated sample processing systems are often limited to only DNA extraction or protein extraction through specific processing steps, with little ability to quickly exchange extraction chemistry or alter processing steps to fit the needs of a particular laboratory. In other words, current systems are not dynamically based on sensed sample input type, e.g., blood, plasma or saliva.

Previously known automated sample processing systems also produced substantial solid or liquid waste, such as used pipette tips or blood extractions, which must be separately processed or disposed of at significant expense, and risks exposing workers to significant hazardous waste.

SUMMARY OF THE INVENTION

Disclosed are high-throughput sample processing systems, components of high-throughput sample processing systems, sample dispensing devices, contactless fluid dispensing devices, contactless treatment stations, contactless liquid level sensors, contactless fluid aspirators, waste management systems, control systems, and a non-transitory computer-readable storage medium for operating a high throughput sample processing system.

In some embodiments, a high throughput sample processing system comprises a sample dispensing device, a plurality of contactless liquid level sensors, a plurality of aspirators, a plurality of contactless treatment stations, a waste management system, and a control system.

In some embodiments, the sample dispensing device can draw a plurality of samples from a plurality of sample containers and dispense each sample into a well of a sample processing plate comprising a plurality of wells. In some embodiments, the sample dispensing device dispenses each sample into a different well. In some embodiments, the sample dispensing device comprises a plurality of syringe based pipettes. In some embodiments, the pipettes comprise reusable pipette tips. In some embodiments, the sample dispensing device comprises a washing station for automatically washing the reusable pipette tips. In some embodiments, the washing station comprises a bleach solution.

In some embodiments, the contactless fluid dispensing device dispenses fluids into the plurality of wells of the sample processing plate.

In some embodiments, the plurality of contactless liquid level sensors detects the liquid level in each of the plurality of wells of the sample processing plate. The liquid level can be determined in a variety of ways, for example, using weight, optical, acoustic, capacitance, or a laser level transmitter. In some embodiments, the liquid level sensors comprise one or more contactless sensors including one or more acoustic sensors, weight sensors, pressure sensors etc. In some embodiments, the liquid level sensors comprise one or more acoustic sensors.

In some embodiments, the plurality of aspirators removes fluids from the plurality of wells of the sample processing plate. In some embodiments, the plurality of contactless treatment stations treats the plurality of sample processing plates simultaneously.

In some embodiments, the waste management system manages fluids removed from the plurality of wells. In some embodiments, the waste management system deposits the fluids removed from the plurality of wells into a waste container. In some embodiments, the waste container operates under a vacuum. In some embodiments, the waste management system mixes the fluids removed from the plurality of wells with a sterilizing solution, e.g., bleach, in the waste container and incubates the mixture. In some embodiments, the waste management system comprises one or more scales for determining an amount of fluids removed from the plurality of wells. In some embodiments a variety of sensors may be used to determine the amount of fluids in the waste management system. The sensors may include, for example, acoustic sensors, weight sensors, pressure sensors etc. In some embodiments, scales are used for determining the amount of fluids removed under vacuum. In some embodiments, the amount of fluid traveling through the system is monitored, for example, to determine whether there is a leak or error in the system.

In some embodiments, the control system controls the processing of a plurality of plates within the high throughput sample processing system simultaneously. In some embodiments, the control system dynamically controls the processing of a plate depending upon the location or status of other plates in the system.

In some embodiments, the high-throughput sample processing system comprises a plate loading device for automatically loading additional plates into the sample dispensing device.

In some embodiments, the high-throughput sample processing system process a plurality of samples, wherein the plurality of samples comprise a bodily fluid. In some embodiments the plurality of samples include blood, saliva, or plasma. In some embodiments, the sample containers are sealed and the pipettes are configured to draw the plurality of samples through seals of the containers. In some embodiments, the high throughput sample processing system extracts DNA from the plurality of samples using magnetic beads.

In some embodiments, the plurality of contactless treatment stations comprise one or more mixing devices. In some embodiments, the one or more mixing devices comprises one or more orbital shakers. In some embodiments, the plurality of contactless treatment stations comprise one or more heating or cooling devices.

In some embodiments, the high throughput sample processing system comprises a barcode scanner for identifying samples using barcodes on the sample containers.

In some embodiments, a high throughput sample processing method comprises drawing a plurality of samples from a plurality of sample containers; dispensing each sample into a well of a sample processing plate comprising a plurality of wells, wherein each sample is dispensed into a different well; dispensing fluids into the plurality of wells of the sample processing plate using a contactless fluid dispensing device; detecting the liquid level in each of the plurality of wells of the sample processing plate using a plurality of contactless liquid level sensors; mixing a plurality of sample processing plates simultaneously using a plurality of contactless mixing devices; removing fluids from the plurality of wells of the sample processing plate using a plurality of aspirators; and managing fluids removed from the plurality of wells using a waste management system.

In some embodiments, a high throughput sample processing method comprises dynamically controlling the processing of a plate depending upon the location or status of other plates. In some embodiments, a high throughput sample processing method comprises automatically loading additional plates into the sample dispensing device.

In some embodiments of a high throughput sample processing method, the plurality of samples comprise blood or saliva. In some embodiments, a high throughput sample processing method comprises extraction of DNA from the plurality of samples using magnetic beads.

In some embodiments of a high throughput sample processing method, the samples are dispensed using a plurality of syringe based pipettes. In some embodiments, the pipettes comprise reusable pipette tips. In some embodiments, a high throughput sample processing method comprises automatically washing the reusable pipette tips. In some embodiments, the pipette tips are automatically washed using a bleach solution.

In some embodiments of a high throughput sample processing method, the liquid level sensors comprise one or more acoustic sensors.

In some embodiments of a high throughput sample processing method, the waste management system deposits the fluids removed from the plurality of wells into a waste container. In some embodiments, the waste container operates under a vacuum. A series of valves may be included to ensure the proper operation of vacuum. In some embodiments the waste is removed using gravity. In some embodiments, the waste management system mixes the fluids removed from the plurality of wells with bleach in the waste container and incubates the mixture. In some embodiments, the waste management system comprises one or more sensors for determining an amount of fluids removed from the plurality of wells. These sensors may include, for example, acoustic sensors, weight sensors, pressure sensors etc. In some embodiments, the waste management system comprises one or more scales for determining an amount of fluids removed from the plurality of wells using a vacuum.

In some embodiments of a high throughput sample processing method, the plurality of contactless mixing devices comprises one or more orbital shakers.

In some embodiments, a high throughput sample processing method comprises scanning with a barcode scanner on the sample containers to identify the samples.

The system is configured to be dynamic. This means that the system can change the scheduling and/or control the processing of samples according to changing values in the system. These changing values can include, for example, the location of other sample processing plates in the system, the type of sample, and the type of process being performed (for example, the type of assay, extraction, and/or treatment).

In some embodiments, a non-transitory computer-readable storage medium for operating a high throughput sample processing system comprises instructions for dynamically scheduling multiple sample processing plates for processing through a sample processing system, wherein the scheduling depends upon the location or status of other sample processing plates in the sample processing system; controlling one or more robotic mechanisms for transferring sample processing plates among devices within the sample processing system; operating a sample dispensing device operable for drawing a plurality of samples from a plurality of sample containers and for dispensing each sample into a well of a sample processing plate comprising a plurality of wells, wherein each sample is dispensed into a different well; operating a contactless fluid dispensing device operable for dispensing fluids into the plurality of wells of each of the sample processing plates; operating a plurality of contactless liquid level sensors operable for detecting the liquid level in each of the plurality of wells of each of the sample processing plates; operating a plurality of aspirators for removing fluids from the plurality of wells of each of the sample processing plates; operating a plurality of contactless mixing devices for mixing a plurality of sample processing plates simultaneously; and operating a waste management system for managing fluids removed from the plurality of wells. In some embodiments, the scheduling depends on a sample type, for example blood, saliva, etc. In some embodiments, the instructions for controlling one or more robotic mechanisms for transferring sample processing plates among devices within the sample processing system do so according to the dynamic scheduling. In some embodiments, the instructions include dynamic error recovery instructions. These instructions may include instructions for controlling one or more robotic mechanisms for correcting errors in the system. For example, the system may identify and self-address certain issues (e.g., a clot in the pipette tip, insufficient aspiration of fluid off of the sample, etc.) before sounding an alarm for human intervention.

In some embodiments, a waste management system for processing waste produced by a high-throughput sample processing system comprises a gravity-based liquid waste input, a vacuum-based liquid waste input, a sterilizing fluid container, two or more liquid waste containers, and one or more scales for determining the amount of liquid waste collected by the one or more liquid waste containers. In some embodiments, the liquid waste containers are configured to alternatively accept liquid waste, treat the liquid waste with a sterilizing fluid, and incubate the sterilizing fluid in the liquid waste for a predetermined period of time before disposing of the treated liquid waste.

BRIEF DESCRIPTION OF THE DRAWINGS

FIG. 3 illustrates an embodiment of a sample dispensing device.

DETAILED DESCRIPTION

Figure 1:
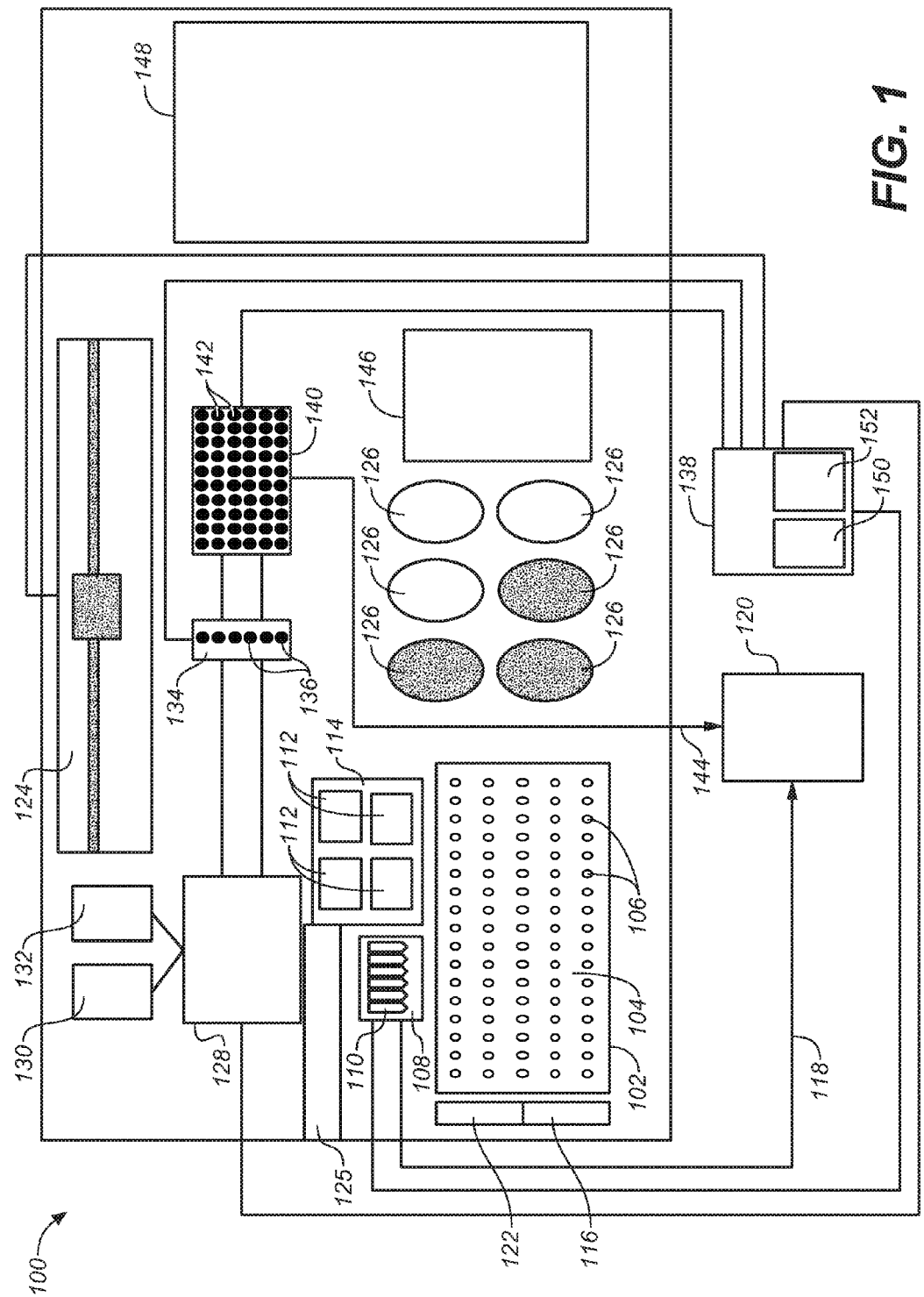
FIG. 1 illustrates one embodiment of a high-throughput sample processing system.

Described are high-throughput sample processing systems, and methods of using such systems. These systems can be used for conducting assays, purifying and/or isolating compounds, and treating samples. Also described are components of such high-throughput sample processing systems, including integrated contactless treatment stations (such as mixing devices and incubation stations), fluid dispensing systems, fluid aeration systems, fluid aspirating systems, liquid level detection systems, and waste management systems, as well as methods of using, controlling, and cleaning such systems.

In some embodiments, the high-throughput sample processing systems can be integrated with other systems, such as assaying, imaging, or final sample processing systems, to form complete contactless research and diagnostic laboratory systems. These high-throughput systems are faster, more cost-efficient, and produce less waste than previously known systems. Furthermore, the high-throughput systems have a more flexible workflow, allowing them to be readily optimized to suit the varying needs of a high-throughput sample processing system operator.

In some embodiments, the high-throughput sample processing systems are designed to continuously receive and process sample sets such that a second sample set can begin a process while a first sample set is in an intermediate stage of the same or different process. A control system can schedule each sample in the system such that no sample interferes with any adjacent sample by utilizing parallel work step setups. In this manner, samples do not need to wait for the preceding sample to complete a specified work step.

In some embodiments, the high-throughput sample processing system is further designed to minimize solid and liquid waste by utilizing contactless devices for dispensing, aerating, mixing, and aspirating fluids. Directly contacting the sample results in contaminated equipment, which must be properly sterilized or disposed to prevent contamination of the sample. For example, disposal of a pipette tip each time a fluid is dispensed, aerated, mixed, or aspirated results in significant solid waste. Solid and liquid waste can be expensive or difficult to dispose of because of the presence of biologically active elements. By minimizing contact with the sample through contactless dispensing, aerating, mixing, or aspirating of fluids, solid waste and sample contamination can be minimized.

Although contact with the sample is minimized in a high-throughput sample processing system, in some embodiments, contact with the sample may still be made. For example, in some embodiments, a sample dispensing device may transfer a sample from a sample tube to a sample processing plate by withdrawing the sample into a pipette tip or needle and dispensing the sample onto the sample processing plate. Additionally, in some embodiments, fluids aspirated from samples may be contaminated. A high-throughput sample processing system therefore may include a waste management system capable of treating and, in some embodiments, disposing of or containing the waste.

To maintain precision between sample preparations, thereby increasing processing reliability, fluids should be consistently dispensed during sample processing. To ensure consistent fluid dispensing and improve processing reliability, some embodiments of the high-throughput sample processing system include a contactless liquid level sensor. A contactless liquid level sensor can signal to a control system when sufficient fluid has been dispensed into a sample such that the sample is at a predetermined volume. In some embodiments, the liquid level sensor detects the sample liquid level without directly contacting the sample. In some embodiments, the liquid level sensor may simultaneously signal to the contactless fluid dispensing device when the contactless fluid dispensing device should continue dispensing fluid and/or when the contactless fluid dispensing device should stop dispensing fluid.

In some embodiments, each work step in a process may be a distinct step or event in a complete process, and may use one or more components of the high throughput system. For example, in some embodiments, a work step may be a sample loading step, an incubating step, a mixing step, a heating step, a solution dispensing step, a solution aerating step, or a solution aspirating step. In some embodiments, a work step may include two or more simultaneous events, such as simultaneous mixing and heating steps, or simultaneous incubating and heating steps. In some embodiments, a work step may include multiple linear or simultaneous smaller work steps, for example, a cell lysis step may include a solution dispensing step, a simultaneous mixing and heating step, and a solution aspirating step. Other work steps may include, but are not limited to, a wash step, an imaging step, a weighing step, a drying step, a freezing step, a lyophilizing step, or an enzymatic reaction step.

Any number of fluid solutions may be used in processing a sample in a high-throughput sample processing system. For example, a fluid solution includes a suspension solution, deionized water, non-deionized water, a lysis solution, a wash solution, an elution solution, an assay solution, or a reactive reagent. In some embodiments, the liquid solution may comprise salts, buffers (e.g., acetate, citrate, bis-tris, carbonate, CAPS, TAPS, bicine, tris, tricine, TAPSO, HEPES, TES, MOPS, PIPES, cacodylate, SSC, MES, succinic acid, or phosphates), amino acids, acids, bases, surfactants, detergents (e.g., SDS, triton X-100, or Tween-20), chaotropic agents, chelators (e.g., ethylenediaminetetraacetic acid, phosphonates, or citric acid), preservatives, antibiotics, alcohols (e.g., methanol, ethanol, propanol, or isopropanol), reducing compounds, oxidizing compounds, dyes, or biomolecules (e.g., nucleic acids, proteins, enzymes (e.g., RNAase or Proteinase K)).

High-Throughput Sample Processing System

In some embodiments, a high-throughput sample processing system includes at least one sample dispensing device, contactless fluid dispensing device, contactless liquid level sensor, contactless fluid aspirator, contactless treatment station, waste management system, and control system. In some embodiments, a plurality of identical components of the high-throughput sample processing system may be used. In some embodiments, one or more plate loading devices, contactless mixing devices, contactless heating devices, contactless incubating devices, contactless cooling devices, contactless freezing devices, contactless lyophilizing devices, weighing devices, or assay or measuring devices may be included in the high-throughput sample processing system. In some embodiments, a robotic arm, belt, sled, or drawer may be used to transfer sample processing plates from one station of the high-throughput sample processing system to a second station of the high-throughput sample processing system.

A high-throughput sample processing system is able to accept a sample input and produce a sample output. In some embodiments, a high-throughput sample processing system may accept any number of sample inputs, including, but not limited to, biomolecules, nucleic acid (including DNA or RNA), proteins, peptides, antibodies, antibody fragments, antibody-small molecule conjugates, enzymes, metabolites, structural proteins, tissues, seeds, cells, organelles, membranes, blood, plasma, saliva, urine, semen, oocytes, skin, hair, feces, cheek swabs, organic molecules, pharmaceutical compounds, bacteria, viruses, or nanoparticles. The output of a high-throughput may be any one of the aforementioned sample input types, in addition to, but not limited to, images, spectroscopy measurements (such as calorimetric, fluorescence measurements, light absorbance, nuclear magnetic resonance, infrared, light scattering spectroscopy, etc.), enzymatic measurements (such as dissociation constants, catalytic rates, $k_{on}$ rates, $k_{off}$ rates, etc.), or a target molecule (such as DNA, RNA, protein, peptide, or organic compound).

In some embodiments, a high-throughput sample processing system can be configured to accept a variety of sample containers, for example a plurality of single tubes, a 6-well plate, a 12-well plate, a 24-well plate, a 48-well plate, a 96-well plate, a 192-well plate, a 384-well plate, a 1536-well plate, or a multiwell plate capable of holding any number of separated samples. In some embodiments, each sample container is identified with a unique identifier such as a barcode. In some embodiments, the sample containers can be capped or sealed, for example by a rubber stopper.

In some embodiments, the high-throughput sample processing system can be configured to utilize a variety of sample processing plates, including a 6-well plate, a 12-well plate, a 24-well plate, a 48-well plate, a 96-well plate, a 192-well plate, a 384-well plate, a 1536-well plate, or a multiwell plate capable of holding any number of separated samples. In some embodiments, maximum well volume of the sample processing plate may be about 18 microliters, about 250 microliters, about 1.1 milliliters, about 2.2 milliliters, about 5 milliliters, or about 10 milliliters. In some embodiments, each sample processing plate is identified with a unique barcode. In some embodiments, the sample processing plate may be pre-loaded with a fluid, such as a lysis fluid, stabilizing fluid, wash fluid, deionized water, or ethanol prior to adding a sample.

In some embodiments, each sample well of the sample processing plate comprises affinity beads that can bind to a target molecule within the sample. For example, the affinity beads may be coated in antibodies, streptavidin, or cationic or anionic moieties. In some embodiments, the affinity beads are magnetic. In some embodiments, affinity beads are pre-loaded into the sample processing plate prior to dispensing of the sample into the sample processing plate. In some embodiments, affinity beads are not pre-loaded into the sample processing plate.

FIG. 1 provides a schematic of one embodiment of a high-throughput sample processing system 100. Sample containers comprising samples intended for system processing are placed in the sample container station 102. In some embodiments, the sample containers can automatically be place in the sample container station from storage using a robotic arm or other automated sample transportation device such as a belt, sled or drawer. In some embodiments, a sample guard 104 is disposed directly above the sample container station 102, holding the sample containers in place. In some embodiments, the sample guard 104 comprises a plurality of sample ports 106, which are wide enough to permit the passage of a pipette but narrow enough to prevent the passage of a sample container cap or seal. In some embodiments, a sample transfer device 108 is disposed adjacent to the sample container station 102, and comprises a plurality of syringe based pipettes 110. When in operation, sample transfer device 108 positions the syringe based pipettes 110 over the sample ports 106, lowers the syringe based pipettes 110 through the sample ports 106, thereby entering the sample containers, and draws a plurality of samples into the syringe based pipettes 110. In some embodiments, the syringe based pipettes 110 pierces the cap or plug of a sample container when being lowered into the sample containers. The system may then repeatedly draw and eject liquid from the sample container using the pipettes 110 to mix samples that may have settled, for example, blood. Once mixing, if any, is completed samples are drawn into the syringe based pipettes 110, the sample transfer device 108 then lifts the syringe based pipettes 110 from the sample containers and dispenses samples into a sample processing plate 112 located in a sample processing plate load tray 114. In some embodiments, the sample guard 106 prevents the syringe based pipettes 110 from removing the cap or plug in the sample containers when the syringe based pipettes 110 are removed from the sample containers. A robotic arm or other transportation device, such as a belt, sled or drawer, can automatically place the sample processing plates into the system from a plate storage area.

In some embodiments, once the sample transfer device 108 has dispensed the sample into the sample processing plate 112, the syringe based pipettes 110 are sterilized prior to reuse. The liquid level of a sample dispensed into the plate can be determined by the system, for example, using weight, digital imaging, ultrasonic, capacitance, or a laser level transmitter. The liquid level may be adjusted if necessary. In some embodiments, to sterilize the syringe based pipettes 110, the sample transfer device 108 lowers the syringe based pipettes 110 into a wash station, which comprises a cleaning solution 116, for example a bleach, hydrogen peroxide, iodine, or ethanol solution, and draws the cleaning solution 116 into the syringe based pipettes 110. In some embodiments, the drawn cleaning solution 116 can continue through a first waste conduit 118 under vacuum pressure for disposal in a waste management system 120. In other embodiments, the cleaning solution 116 can be deposited into a waste collection trap connected to the first waste conduit 118, which flows to the waste management system 120 under gravity forces. Similarly, the syringe based pipettes 110 can be rinsed in deionized water 122, which is drawn into the syringe based pipettes 110 and disposed of in the waste management system 120 via the first waste conduit 118. Once sterilized and rinsed, the syringe based pipettes 110 may be reused to draw a new sample.

In some embodiments, once a plurality of samples have been dispensed into the sample processing plate 112, a robotic arm 124, or other robotic transportation device such as a belt, sled, or drawer, can retrieve the sample processing plate 112 and transport it to the next intended high-throughput processing system 100 component. In some embodiments, once the sample processing plate 112 has been removed from the sample processing plate load tray 114, a plate loading device 125 automatically loads a new sample processing plate 112 onto the sample processing plate load tray 114.

In some embodiments, the robotic arm 124 or other robotic transportation device such as a belt, sled, or drawer, transports the sample processing plate 112 to a sample treatment station 126. In some embodiments, the high-throughput sample processing system 100 has one or more sample treatment stations 126 of the same type or of different types. In some embodiments, the sample treatment station 126 may be heated, chilled, or set to ambient temperature. In some embodiments, a sample treatment station 126 may provide contactless mixing of the sample, while in some embodiments a sample treatment station 126 may be stationary. In some embodiments, the sample treatment station 126 may provide both heating and contactless mixing of the sample. In some embodiments, the sample treatment station 126 may provide both cooling and contactless mixing of the sample. In some embodiments, the sample treatment station 126 may be an orbital shaker, a heating block, or a refrigeration block.

In some embodiments, the robotic arm 124 or other robotic transportation device such as a belt, sled, or drawer, transports the sample processing plate 112 to a contactless fluid dispensing device 128. The contactless fluid dispensing device 128 is disposed to provide a predetermined amount of fluid into each well of the sample processing plate 112. In some embodiments, the contactless fluid dispensing device 128 is configured to dispense a single type of fluid, while in some embodiments, contactless fluid dispensing device 128 is configured to dispense two or more different types of fluids. For example, in some embodiments, the contactless fluid dispensing device 128 is configured to dispense a high-salt washing fluid 130 and an elution fluid 132. It is contemplated that the contactless fluid dispensing device 128 can be configured to dispense any other type of fluid, for example, but not limited to, a lysis fluid, an alcohol fluid, a denaturing fluid, an enzymatic fluid, magnetic beads as a slurry, a second wash fluid that may be the same or different than the high-salt washing fluid, and/or deionized water.

In some embodiments, the robotic arm 124 or other robotic transportation device such as a belt, sled, or drawer, transports the sample processing plate 112 to a contactless liquid level sensor system 134, which comprises a plurality of liquid level sensors 136. The contactless liquid level sensor system 134 detects the liquid level of each well of the sample processing plate 112 and transmits this data to a control system 138.

When the fluid dispensing device is used to dispense a slurry comprising magnetic beads a magnetic bead recirculation pump can be used to keep the beads suspended in the slurry prior to dispensing as the beads can settle out if they are not continuously stirred. The magnetic bead recirculation pump preferably does not include any metal contacts that would attract the magnetic beads. In some embodiments, a continuous recirculating pump with a diaphragm pump with all plastic wetted ports is used.

In some embodiments, the robotic arm 124 or other robotic transportation device such as a belt, sled, or drawer, transports the sample processing plate 112 to a contactless fluid aspirating system 140, comprising a plurality of contactless fluid aspirators 142. In some embodiments, the contactless fluid aspirating system 140 is immediately adjacent to the contactless liquid level sensor system 134 such that the liquid levels are measured while the sample processing plate 112 is being positioned into the contactless fluid aspirating system 140. The contactless fluid aspirators 142 use suction forces to simultaneously siphon fluid from each sample well in the sample processing plate 112. In some embodiments, the suction force is provided by the waste management system 120, which can also receive aspirated fluid via the second waste conduit 144. In some embodiments, the suction force is strong enough to aspirate fluid from the sample wells without making contact with the samples themselves. In some embodiments, the contactless fluid aspirating system 140 lowers the plurality of contactless fluid aspirators 142 into the sample wells at a rate to maintain sufficient suction force against the sample to aspirate fluid but without causing contact with the sample.

At the completion of sample processing, the robotic arm 124 or other robotic transportation device such as a belt, sled, or drawer, can transport the sample processing plate 112 to the sample output station 146. In some embodiments, once the sample processing plate 112 is transported to the sample output station 146, it may be collected by a technician. In some embodiments, the processed sample processing plate may be transported directly to an analytical or final processing device 148. For example, in some embodiments, an analytical device 148 may be an imager, spectrometer, or scale. In some embodiments, a final processing device 148 may be a heating, freezing, lyophilizing device.

In some embodiments, a high-throughput sample processing system 100 comprises a control system 138 for controlling a plurality of simultaneously processed sample processing plates 112, receiving barcode data and liquid level measurements, or system monitoring (including fluid levels, vacuum pressures, or temperatures). In some embodiments, the control system 138 comprises one or more microprocessors 150 and a non-transitory computer readable storage medium 152. In some embodiments, the control system 138 dynamically schedules multiple sample processing plates 112 depending on the location or status of the multiple sample processing plates 112. In some embodiments, the control system 138 receives multiple sample processing plates 112 location data from transmitted barcode readings in the various components of the high-throughput sample processing system 100.

In some embodiments, the control system 138 controls one or more robotic mechanisms for transferring sample processing plates 112, for example a robotic arm 124, drawer, sled, or belt. In some embodiments, the control system 138 controls a sample dispensing device 108 to dispense samples into a plurality of wells in a sample processing plate 112. In some embodiments, the control system 138 simultaneously controls the temperature or mixing speed of one or more contactless treatment stations 126, for example one or more contactless mixing devices, heating devices, or cooling devices. In some embodiments, the control system 138 controls a contactless fluid dispensing device 128 by indicating type and quantity of fluid to be dispensed into the wells of the sample processing plate 112. In some embodiments, the control system 138 controls a contactless liquid level sensor system 134 and calculates the liquid level of a plurality of wells in a sample processing plates 112 by receiving data from the contactless liquid level sensor system 134. In some embodiments, the control system 138 controls a contactless fluid aspirating system 140, and in some embodiments the microprocessor can control return of a sample processing plate 112 to the contactless fluid aspirating system 140 based on data received from the contactless liquid level sensor system 134. In some embodiments, the control system 138 can control one or more analytical or final processing devices 148. In some embodiments, the control system 138 controls a waste management system 120.

In some embodiments, a non-transitory computer readable storage medium 152 comprises instructions for operation of one or more microprocessors 150 or control system 138. In some embodiments, the non-transitory computer readable storage medium 152 comprises instructions for dynamically scheduling multiple sample processing plates 112 depending on the location or status of the multiple sample processing plates 112 within the high-throughput sample processing system 100.

The control system may also control dynamic error recovery. For example, the system may identify when errors are present in the system and attempt to self-address the issue before sounding an alarm for human intervention. For example, the system may identify that a clot is in a pipette tip and dynamically schedule additional flushing of this pipette tip. The system may also, for example, increase or decrease the amount of fluid delivered or remove/aspirated.

In some embodiments, the non-transitory computer readable storage medium 152 comprises instructions for controlling one or more robotic mechanisms for transferring sample processing plates 112, for example a robotic arm 124, drawer, sled, or belt. In some embodiments, the non-transitory computer readable storage medium 152 comprises instructions for controlling a sample dispensing device 108, which can draw samples from a plurality of sample containers and dispense samples into a plurality of wells in a sample processing plate 112. In some embodiments, the non-transitory computer readable storage medium 152 comprises instructions for controlling a contactless fluid dispensing device 128 for dispensing fluid into the wells of the sample processing plate 112. In some embodiments, the non-transitory computer readable storage medium 150 comprises instructions for controlling a contactless liquid level sensor system 134, which can detect the liquid level in each of a plurality of wells in a sample processing plate 112. The liquid level can be determined by the system, for example, using weight, digital imaging, ultrasonic, or a laser level transmitter. In some embodiments, the non-transitory computer readable storage medium 152 comprises instructions for controlling a contactless fluid aspirating system 140. In some embodiments, the non-transitory computer readable storage medium 152 comprises instructions for controlling a waste management system 120. In some embodiments, the non-transitory computer readable storage medium 152 comprises instructions for controlling one or more analytical or final processing devices 148. In some embodiments, the non-transitory computer readable storage medium 152 comprises instructions for simultaneously controlling the temperature or mixing speed of one or more sample treatment stations 126, for example one or more contactless mixing devices, heating devices, or cooling devices.

Figure 2:
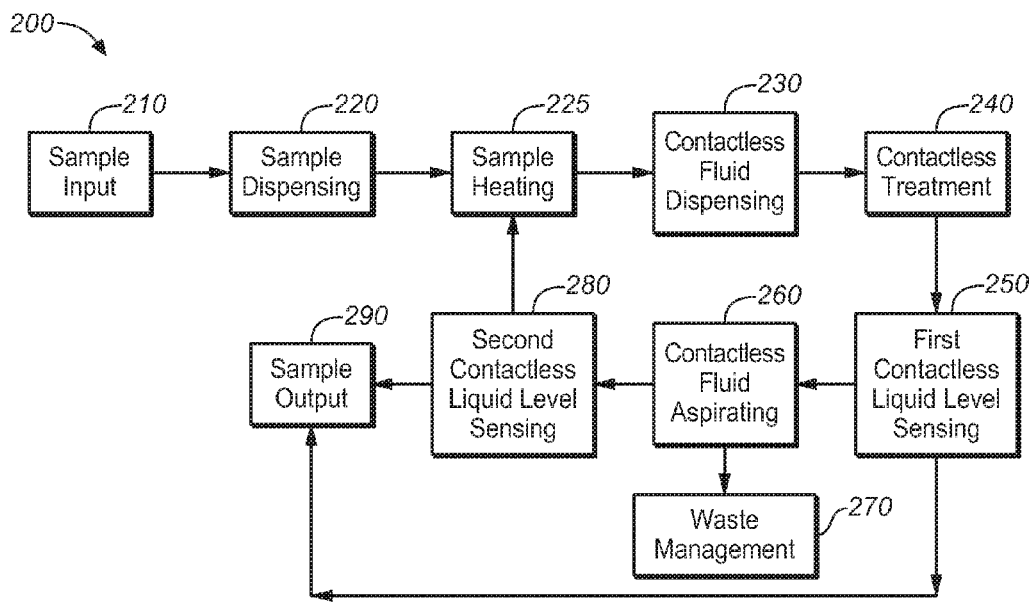
FIG. 2 is a flow chart of a method of processing a sample using a high-throughput sample processing system.

FIG. 2 provides a flowchart illustrating one example method 200 of a high-throughput sample processing system in operation to process a sample. Samples may include a single type of sample or one or more different types of samples including blood, plasma and/or saliva. The system may dynamically control system processing depending upon the sample type(s). At step 210, a technician inputs a plurality of samples in sample containers into the high-throughput sample processing system. Once the plurality of samples have been inputted into the high-throughput sample processing system, the technician need not disrupt the plurality of samples until the sample outputs are collected at step 290. Additionally, in some embodiments, the technician may input more samples into the high-throughput sample processing system than the system is configured to process at any single sample run, as the high-throughput sample processing system may be configured to simultaneously process multiple sample processing plates. For example, in some embodiments, if the high-throughput sample system is configured to process samples dispensed into a 96-well sample processing plate in a single sample run, the system may be configured to allow the technician to load more than 96 samples.

At step 220, a sample dispensing device can simultaneously draw a plurality of samples from the plurality of sample containers and dispense each sample into a plurality of wells in a sample processing plate, such as a multi-well plate, with each separate sample being dispensed into a separate sample well. Once the plurality of samples have been dispensed into the sample processing plate, the sample processing plate can be transported to a contactless fluid dispensing device. After the departure of the sample processing plate from the sample dispensing device, in some embodiments, a plate loading device can automatically reload the sample dispensing device with a new sample processing plate.

At step 225, a contactless heater can be used to heat the plurality of samples to a desired temperature.

At step 230, a contactless fluid dispensing device can dispense a predetermined amount of fluid into the plurality of wells of the sample processing plate. Once the amount of fluid has been added to the sample, the sample processing plate can be transported to the next step of the process.

At step 240, the plurality of samples may be treated to any number of contactless treatment steps. In some embodiments, the plurality of samples undergo one or more of contactless mixing, contactless heating, contactless cooling, or contactless ambient incubation. In some embodiments, contactless mixing is conducted by one or more orbital shakers. Once the contactless treatment step is completed, the sample processing plate can be transported to a contactless liquid level sensor device at step 250. In some embodiments, the sample processing plate may bypass the first contactless liquid level sensing step 250 and be transported directly to a contactless aspirating device at step 260.

At step 250, the level of liquid in each well in the sample processing plate can be measured using a plurality of contactless liquid level sensors in a first contactless liquid level sensing step. In some embodiments, the plurality contactless liquid level sensors can transmit the liquid level of each sample processing plate well to a control system. In some embodiments, if the liquid level sensor detects a liquid level higher than a predetermined level, the control system can terminate system processing or signal an alarm. Once the first contactless liquid level sensing step 250 is complete, the sample processing plate can be transported to a contactless fluid aspirating device.

At step 260, a contactless aspirating device can remove fluid from the sample without withdrawing target molecules. In some embodiments, a plurality of contactless aspirating devices are used to aspirate fluid from each of a plurality of samples within a sample processing plate. In some embodiments, such as when magnetic affinity beads are used to contact target molecules, a magnet can be used to contain target molecules at the base of the sample container while the aspirating device pulls liquid from the top of the sample using suction forces. In some embodiments, the aspirating device does not touch the sample, but suction forces are strong enough to cause fluid to be pulled into the aspirating device. Aspirated fluid can then be transported to a waste management system using a waste conduit in step 270.

At step 270, the waste management system can treat aspirated fluid from step 260 for appropriate liquid waste disposal. In some embodiments, the amount of liquid waste is measured, for example by weighing the liquid waste collected using a scale. In some embodiments, an amount of sterilizing solution, for example bleach, is added to the collected liquid waste to treat the waste. The amount of bleach being dispensed can be monitored using a sensor, for example an acoustic sensor, to ensure the correct volume is dispensed. In some embodiments, the liquid waste and sterilizing solution mixture is allowed to incubate for a predetermined period of time before it is removed from the waste management system, for example by draining into a sewage system. One or more fluid flows in the waste management system can be monitored to ensure that all waste is accounted for in order to detect errors and/or leaks in the system. These fluid flows can be monitored, for example, by sensors that detect pressure, weight and/or volume of the fluid flows.

In some embodiments, after the completion of the contactless fluid aspirating step 260, a second contactless liquid level sensing step 280 allows the plurality of contactless liquid level sensors to determine the level of liquid in each well of the sample processing plate. The level of the liquid in each sample well may be transmitted to the control system where, in some embodiments, the control system can compare the level of liquid in each well during the second contactless liquid level sensing step 280 with the level of the liquid in each well during the first contactless liquid level sensing step 250. An insufficient difference between the liquid levels during the two contactless liquid level sensing steps indicates the contactless fluid aspirating device may be acting improperly, and the control system may terminate sample processing, signal an alarm, or redeploy the sample to the contactless fluid aspirating device for additional fluid aspiration at step 260.

In some embodiments, after the second contactless liquid level sensing step 280, the sample may be transported back to the contactless fluid dispensing system at step 230 for iterative processing. In some embodiments, the iterative processing cycle may be performed one or more times and can be controlled by a control system. At each iterative cycle, the contactless fluid dispensing system may dispense the same or a different fluid as the previously dispensed fluid. Similarly, at each iterative cycle, the contactless treatment step 240 may comprise the same or different contactless treatments. For example, a sample may first be treated with a lysis fluid by a contactless fluid dispensing system at step 230 and heated and mixed using a heated contactless mixer at step 240 in a first iteration, followed by the sample being treated with a wash fluid at step 230 and cooled and mixed using a chilling contactless mixer at step 240 in a second iteration. In some embodiments, to ensure proper functioning of the contactless aspirating device and avoid unintentional overfilling of the sample processing plate wells, the liquid level of the sample wells can be determined in steps 250 and 280 during each iteration and transmitted to the control system.

In some embodiments, after the final contactless liquid level sensing step 280, the sample output is made available in step 290. In some embodiments, the final contactless liquid level sensing step is step 250 and not step 280, for example after iterative processing when no further fluid aspiration is necessary. In such an embodiment, the sample processing plate can be transported to the sample output at step 290 after completion of the contactless liquid level sensing step 250. In some embodiments, the sample output is made available to a technician for collection or further processing. In some embodiments, the sample output is automatically transferred to another robotic station or system for further processing. In some embodiments, the further processing includes freezing, lyophilizing, assaying, and/or imaging. In some embodiments, the samples may be transferred to another tray at a magnetic station to separate the samples from any magnetic beads prior to further processing.

The steps of the high-throughput sample processing system 100 can be dynamically scheduled by a control system to ensure correct processing sequence and coordinating a plurality simultaneously processed sample processing plates. In some embodiments, 1 or more, 2 or more, 3 or more, 4 or more, 5 or more, 6 or more, 7 or more, 8 or more, 9 or more, or 10 or more sample processing plates can be simultaneously processed. In some embodiments, for example, a first sample processing plate may undergo a contactless mixing at step 240 while a second sample processing plate is receiving fluid from the contactless fluid dispensing system at step 230. In some embodiments, a first sample processing plate may undergo a contactless mixing at step 240 with no further iterative processing steps while a second sample processing plate is simultaneously undergoing a contactless mixing at step 240 by a separate contactless mixer with an additional iterative processing step before the sample is outputted.

In some embodiments, one or more of the sample dispensing system devices, the contactless fluid dispensing device, the contactless treatment stations, the contactless liquid level sensor system, the contactless fluid aspirator, or the sample output station comprise a barcode scanner that is configured to read a barcode on a sample container or sample processing plate to assign a location to the sample container or sample processing plate, and transmit this location to the control system. In some embodiments, the control system may then log the location, initiated process step, or completed process step of each sample container or sample processing plate and determine the next process step for each sample or sample processing plate based on its location and previously completed process step. The control system is therefore able to balance the steps of each of the simultaneously processed samples and sample processing plates.

In some embodiments, two or more sample processing plates may be simultaneously processed at the same processing step, although the sample processing plates may be undergoing different iterations of the same processing step. For example, a first processing plate may be undergoing a contactless treatment step, for example contactless mixing, when a second processing plate is scheduled to initiate a contactless treatment step, for example contactless mixing. In some embodiments, a control system is able to balance the contactless treatment step by determining the location of the first processing plate at a first contactless treatment station and controlling a robotic arm, belt, sled, or drawer to transport the second processing plate to a second contactless treatment station. The control system can therefore schedule multiple sample processing plates such that the sample processing plate is transported to a vacant location rather than an occupied location.

By dynamically balancing multiple sample processing plates, a high-throughput sample processing system can have significantly increased throughput with significantly reduced waste and smaller system footprint. In some embodiments, a high-throughput sample processing system can process more than about 480 samples per day, more than about 960 samples per day, more than about 1440 samples per day, more than about 1920 samples per day, more than about 2100 samples per day, or more than about 2580 samples per day.

Sample Dispensing Device

A sample dispensing device can transfer a plurality of samples from a plurality of sample containers to a plurality of wells of a sample processing plate. The dispensed samples can then continue to be processed by the high-throughput sample processing system while additional samples are dispensed into a new sample processing plate. In some embodiments, the sample dispensing device comprises a sample transfer device, one or more syringe based pipettes (and/or other dispensing devices such as peristaltic pump, centrifugal pumps, microannuler pumps, etc.), a sample guard, and a wash station. In some embodiments, the sample dispensing device comprises a plate loading device to reload sample processing plates. In some embodiments, the sample dispensing device comprises a barcode scanner.

FIG. 3 illustrates one embodiment of a sample dispensing device 300. In some embodiments, the inputted samples containers 302 are placed in a sample container bay 304. The inputted sample containers comprise separate tubes, which may be capped or sealed, for example by a rubber stopper 306. In some embodiments, the samples are under vacuum pressure within the sample containers. In some embodiments, a barcode 308 is provided on each sample container 302, which can be scanned by a barcode scanner. In some embodiments, a barcode scanner is configured to scan a barcode on a sample processing plate 310, scan a barcode on a plurality of sample containers, and assign a sample well location within the sample processing plate 310 to each sample. The barcode can me placed anywhere on the container 302, for example, on the side or bottom of the container 302. A variety of different barcodes may be used including one and two dimensional barcodes. In some embodiments, the barcode scanner transmits the sample well location of each sample to a control system. This allows the control system to record and monitor the location of each sample once dispensed by the sample dispensing device 300 into a sample processing plate 310. In some embodiments, the order of samples in the system may not matter as the sample barcodes are checked against a database allowing the system to know the type of sample (saliva, blood plasma etc.), the type of sample assay to run, and the location of the sample in the system.

In some embodiments, a sample dispensing device 300 comprises a sample transfer device 312 configured with a plurality of syringe based pipettes 314. In some embodiments, sample transfer device controls a piston, which when drawn allows the syringe based pipettes 314 to draw a sample. In some embodiments, the sample transfer device can lower the plurality of syringe based pipettes 314 into the sample containers 302 to access a sample. In some embodiments, the syringe based pipettes 314 pierce a sample container cap or seal 306 to access the sample. The sample transfer device 312 can activate the syringe based pipettes 314 drawing the sample into the pipette, and subsequently the pipette can be raised out of the sample container 302.

In some embodiments, a sample guard 316 can be placed over the sample containers to prevent the sample container cap or seal 306 from being dislodged while the syringe based pipettes 314 are being raised by the sample transfer device 312. In some embodiments, the sample guard 316 has an opening large enough to allow the pipette to pass but not so large as to allow displacement of the sample container cap or seal 306. In some embodiments, a system operator can readily exchange the sample guard 316 to accommodate different size sample containers. For example, in some configurations the sample guard 316 is designed to accommodate wide sample containers 302, such as those commonly used for saliva collection, while in other configurations the sample guard is designed to accommodate narrower sample containers 302, such as those commonly used for blood collection. Easy exchange of the sample guard 316 increases the versatility of the high-throughput sample processing system, allowing it to accommodate a variety of input sample containers 302.

Once the sample transfer device 312 has drawn a sample from a sample container, the sample transfer device 312 can dispense the sample into a defined location within a sample processing plate 310. In some embodiments, the sample processing plate is pre-loaded with a fluid, such as a lysis fluid, stabilizing fluid, wash fluid, deionized water, or ethanol solution prior to adding a sample. In some embodiments, the sample dispensing device may mix the dispensed sample with a pre-loaded fluid, for example by aspirating and redispensing the mixture.

Previous sample processing systems provided for disposable pipettes to dispense samples, resulting in significant solid waste. In some embodiments of the high-throughput sample processing system, the syringe based pipettes 314 are reusable. In some embodiments, after the sample transfer device 312 has dispensed a sample into the sample processing plate the syringe based pipettes 314 are automatically washed at a washing station 318. In some embodiments, a washing station may comprise a cleaning solution 320 and deionized water 322. Preferably, the cleaning solution 320 is a bleach solution, however any solution that can clean or sterilize the pipettes may be used, including hydrogen peroxide, iodine, or alcohol solutions. Solutions used for cleaning the syringe based pipettes pipettes can be disposed of in a waste container 324, which is fluidly connected to a the waste management system.

In some embodiments, the sample dispensing device 300 can be configured to utilize any type of multiwell sample processing plate 310. Once the sample dispensing device has completed dispensing samples on the sample processing plate 310, the loaded sample processing plate can be transported to the next step of processing. In some embodiments, a plate loading device 326 can automatically reload the sample dispensing device with a new sample processing plate 310.

Figure 4:
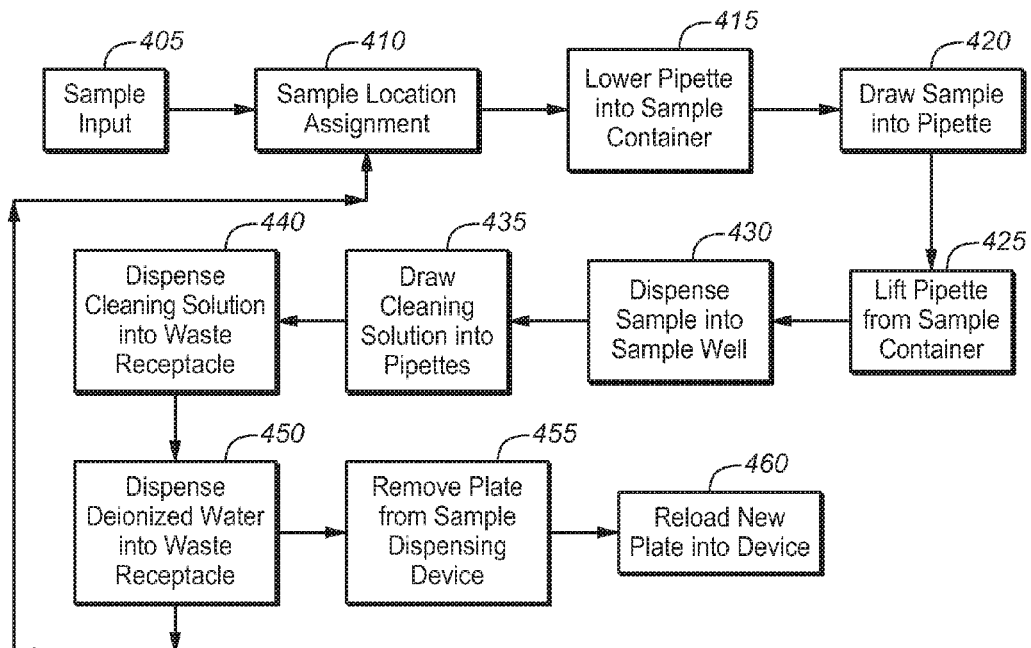
FIG. 4 is a flow chart of a method of operating a sample dispensing device.

FIG. 4 illustrates one example method of operating a sample dispensing device. At step 405, a laboratory technician, robotic arm, or other automated loading device loads a plurality of sample containers into an input station of the sample dispensing system. In some embodiments, a sample guard may be placed over the plurality of sample containers to prevent displacement of a sample container seal or cap.

At step 410, a barcode scanner scans a barcode on a sample processing plate, scans a barcode on a first sample container amongst a plurality of sample containers, and assigns the sample to a sample well on the sample processing plate. The sample location is then transmitted to a control system.

At step 415, a syringe based pipette is lowered into the sample container, and, in some embodiments, pierces through the sample container cap or seal. In some embodiments, a plurality of syringe based pipettes are simultaneously lowered into a plurality of sample containers.

At step 420, a sample transfer device pulls a syringe plunger in the syringe, drawing a predetermined amount of sample from the sample container into the pipette. In some embodiments, a plurality of samples are simultaneously drawn into a plurality of pipettes. In some embodiments, the samples are mixed prior to drawing a sample into the pipette. For example, blood samples may need to be mixed because of settling. The samples may be mixed using the pipettes, for example by repeatedly drawing and ejecting a portion of the sample using the pipettes. In some embodiments, the sample containers are mixed using an orbital shaker or other contactless mixing device. In some embodiments, the drawn sample is about 25 microliters or less, about 50 microliters or less, about 100 microliters or less, about 150 microliters or less, about 275 microliters or less, about 500 microliters or less, or about 1000 microliters or less. In some embodiments, the drawn sample is larger than about 1000 microliters At step 425, the pipette (or plurality of pipettes) loaded with a sample (or plurality of samples) is lifted out of the sample container. In some embodiments, a sample guard prevents the syringe based pipette from dislodging a sample container cap or seal.

At step 430, the sample (or plurality of samples) is dispensed into the sample processing plate according to the location assigned in step 410. In some embodiments, for example where the sample processing plate is pre-loaded with a fluid, the sample may be mixed by drawing the sample back into the pipette and redispensing the sample to the same sample well location one or more times. In some embodiments, the samples are mixed using an orbital shaker or other contactless mixing device. Following the dispensing of the samples the pipettes may be flushed.

At step 435, the pipettes are lowered into a cleaning solution, for example a bleach, hydrogen peroxide, iodine, or ethanol solution, and the cleaning solution is drawn into the pipettes.

At step 440, the cleaning solution is dispensed into a waste receptacle, which is fluidly coupled to a waste management system by a waste conduit. In some embodiments, a single waste receptacle is used. In some embodiments, the dispensed cleaning solution flows to the waste management system under gravity or suction forces. In some embodiments, steps 435 and 440 are repeated one or more times.

At step 450, the pipette tips are flushed by, for example, drawing deionized water into the pipettes and then dispensing the fluid into a waste receptacle, which is fluidly coupled to a waste management system by a waste conduit. In some embodiments, the dispensed deionized water flows to the waste management system under gravity or suction forces. In some embodiments, step 450 is repeated one or more times. In some embodiments, after step 450, the sample dispensing device may continue to load additional samples onto the sample processing plate by returning to step 410. If the sample processing plate is fully loaded with samples or no additional samples are available to be loaded, the sample dispensing device proceeds to step 455.

In some embodiments, at step 455, a robotic arm, belt, sled, or drawer may remove the sample processing plate from the sample dispensing device. In some embodiments, the sample processing plate may proceed to a subsequent step in the high-throughput sample processing system, for example a contactless treatment step, a contactless fluid aspirating step, or a contactless fluid dispensing step.

In some embodiments, at step 460, once the sample processing plate is removed from the sample dispensing device, a plate loading device automatically loads a new sample processing plate into the sample dispensing device.

This process allows a sample dispensing device to transfer samples from a sample container to a sample processing plate while eliminating solid waste. Furthermore, this process allows a location to be assigned to each sample so that a control system can monitor sample progression through the system.

Contactless Fluid Dispensing Device

A contactless fluid dispensing device can dispense fluid into a plurality of wells of a sample processing plate during high-throughput sample processing system operation without contacting fluids already in the wells. In some embodiments, the amount of fluid dispensed is controlled by a control system, and may be predetermined or determined by the control system in response to an earlier liquid level determination. In some embodiments, the contactless fluid dispensing device comprises a barcode scanner, which may read a barcode on a sample processing plate and transmit the location of the sample processing plate to the control system. In some embodiments, the bardcode scanner may not be used at this point in the process as once the samples are initially scanned by the system, the system can determine the location of each sample without further scanning. The contactless fluid dispensing device can dispense fluids based on, for example, the assay and/or extraction method to be used.

Figure 5:
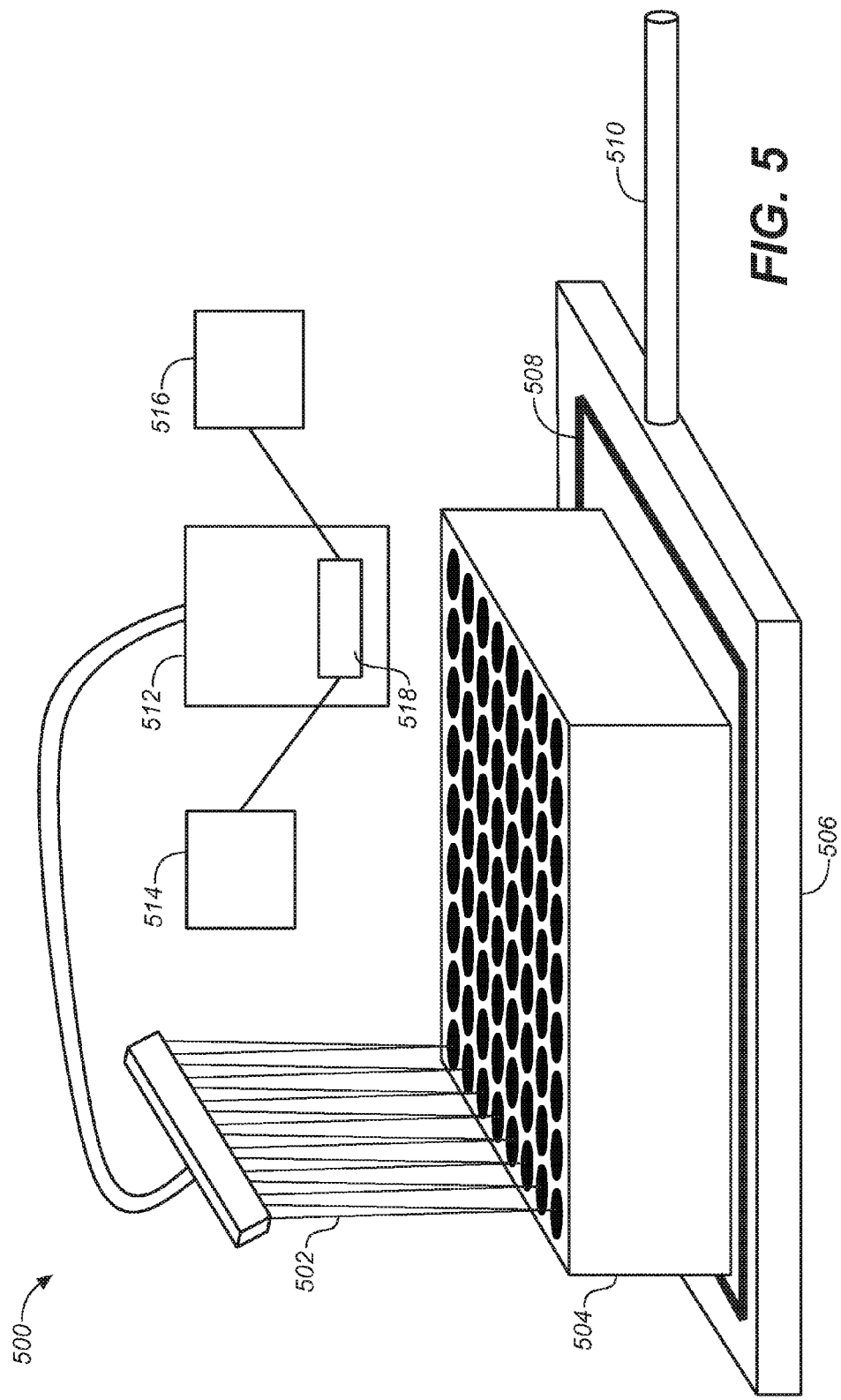
FIG. 5 illustrates an embodiment of a contactless fluid dispensing device.

FIG. 5 illustrates one embodiment of a contactless fluid dispensing device 500. In some embodiments, the contactless fluid dispensing device 500 is configured with one or more fluid dispensing nozzles 502 to dispense fluid into the plurality of wells on the sample processing plate 504. In some embodiments, the sample processing plate 504 can be moved to allow the wells of the plate to be disposed directly underneath the fluid dispensing nozzles 502, for example by use of a drawer or sled, while in some embodiments, the fluid dispensing nozzles can be moved to allow the fluid dispensing nozzles 502 to be disposed directly above the wells of the sample processing plate 504. In some embodiments, the plurality of wells of the sample processing plate 504 receive fluid simultaneously, while in some embodiments, the wells of the sample processing plate receive fluid sequentially.

In some embodiments, the contactless fluid dispensing system 500 comprises a drainage tray 506 disposed underneath the sample processing plate while fluid is being dispensed, which allows collection of any fluid which might accidently overflow from the sample wells. In some embodiments, the drainage tray 506 comprises a waste collection groove 508 fluidly connected to waste management conduit 510, which leads to a waste management system. Overflowed samples as well as waste from priming and purging of the dispensing lines, which may include biohazardous waste, can then be safely disposed by the waste management system without the need for substantial cleanup of the fluid dispensing system 500.

In some embodiments, the contactless fluid dispensing system may be configured to dispense one or more different types of fluid. In some embodiments, the contactless fluid dispensing system may comprise a fluid valve(s) 512. The fluid valves are configured to allow liquid to be pulled from one or more fluid reservoirs 514 and 516. The fluid reservoirs may include a variety of fluids, for example, washes, reagents, rinses etc. The fluids may be pre-mixed before being dispensed. The fluid reservoirs may be scalable according to the volume used in the system and the volume of the source fluid. The scalability of these reservoirs helps allow for unattended operation of the system during operation.

In some embodiments, a pump 518 can draw fluid from a reservoir 514 or 516 to dispense a determined or predetermined amount of fluid into the wells of the sample processing 504 plate via fluidly connected nozzles 502. In some embodiments, two or more pumps 518 draw from two or more different reservoirs 514 and 516 and dispense fluid via the nozzles only after the fluid is mixed by a fluid mixer 512. In some embodiments, the proportion of mixed fluids is controlled by the rate at which fluid is drawn by the separate fluid pumps 518. In some embodiments valves can be included in the system to allow a fluid pump 518 to draw and dispense liquids from multiple fluid reservoirs 514 and 516.

Contactless Treatment Station

Previously known sample processing systems treated or mixed samples by repeated aspirating and dispensing of the sample with disposable pipette tips or stirring with disposable rods or magnetic stir bars placed within the sample. Using these contacting means to treat samples results in substantial solid waste, which must be properly disposed of and/or treated. Some embodiments of a high-throughput sample processing system, as described herein, therefore use one or more contactless treatment stations to mix or otherwise treat samples. The contactless treatment step, such as contactless mixing, does not use magnetic stir bars, disposable rods, or repeated aspiration and solution dispensing to mix the processing samples. This contactless method of treating samples results in significant reduction of waste compared to previously known sample processing systems.

In some embodiments, the contactless treatment station may comprise a contactless mixer, a water bath, a contactless heater, a contactless chiller, or a contactless ambient incubator. In some embodiments, the contactless treatment station may comprise two or more functional elements, such as heated contactless mixing or chilled contactless mixing. In some embodiments, the contactless treatment stations comprise a barcode scanner, which can scan a barcode provided by the sample processing plate and transmit the location of an individual sample processing plate to a control system.

In some embodiments, a contactless mixer is an orbital shaker (such as a high-speed orbital shaker). In some embodiments, the sample processing plate fits into a nest to secure the plate on the contactless mixer. In some embodiments, the contactless mixer rotates at about 50 rotations per minute (rpm) or more, about 250 rpm or more, about 500 rpm or more, about 1000 rpm or more, about 2000 rpm or more, or about 3000 rpm or more.

In some embodiments, the contactless treatment station can be heated using a heating block (such as a dry block heater or a heated water bath) to a temperature of about 25° C. or more, about 30° C. or more, about 37° C. or more, about 45° C. or more, about 65° C. or more, or about 95° C. or more. In some embodiments, the contactless treatment station can be chilled using a chilling block (such as a dry block chiller or an ice bath) to a temperature of about 25° C. or less, about 20° C. or less, about 15° C. or less, about 5° C. or less, about 0° C. or less, or about −5° C. or less, or about −20° C. or less. In some embodiments, the contactless treatment stations comprise a thermometer, and in some embodiments the contactless treatment stations transmit temperature or rotation speed to the control system.

In some embodiments, the contactless treatment station may provide both mixing and heating or both mixing and chilling. For example, the contactless treatment station may be a thermo shaker.

In some embodiments, a high-throughput sample processing system comprises one or more contactless treatment stations. In some embodiments, a high-throughput sample processing system comprises two or more, three or more, or four or more contactless treatment stations. In some embodiments of a high-throughput sample processing system in operation, the contactless sample treatment step is a longer step than other processing steps. For example, in some embodiments, the contactless sample treatment step is longer than the sample dispensing step, the contactless fluid dispensing step, the contactless liquid level sensing step, or the contactless fluid aspirating step.

To prevent a backlog of sample processing plates, in some embodiments of the high-throughput sample processing system, multiple contactless sample treatment stations are operated in parallel. For example, at some periods of time during the high-throughput sample processing system operation, a first sample processing plate undergoes contactless sample processing at a first contactless sample processing station while a second sample processing plate undergoes contactless sample processing at a second contactless sample processing station. Also, at some periods of time during the high-throughput sample processing system operation, a first sample processing plate undergoes contactless sample processing at a first contactless sample processing station while a second contactless sample processing station is idle and awaiting the loading of a second sample processing plate.

Figure 6:
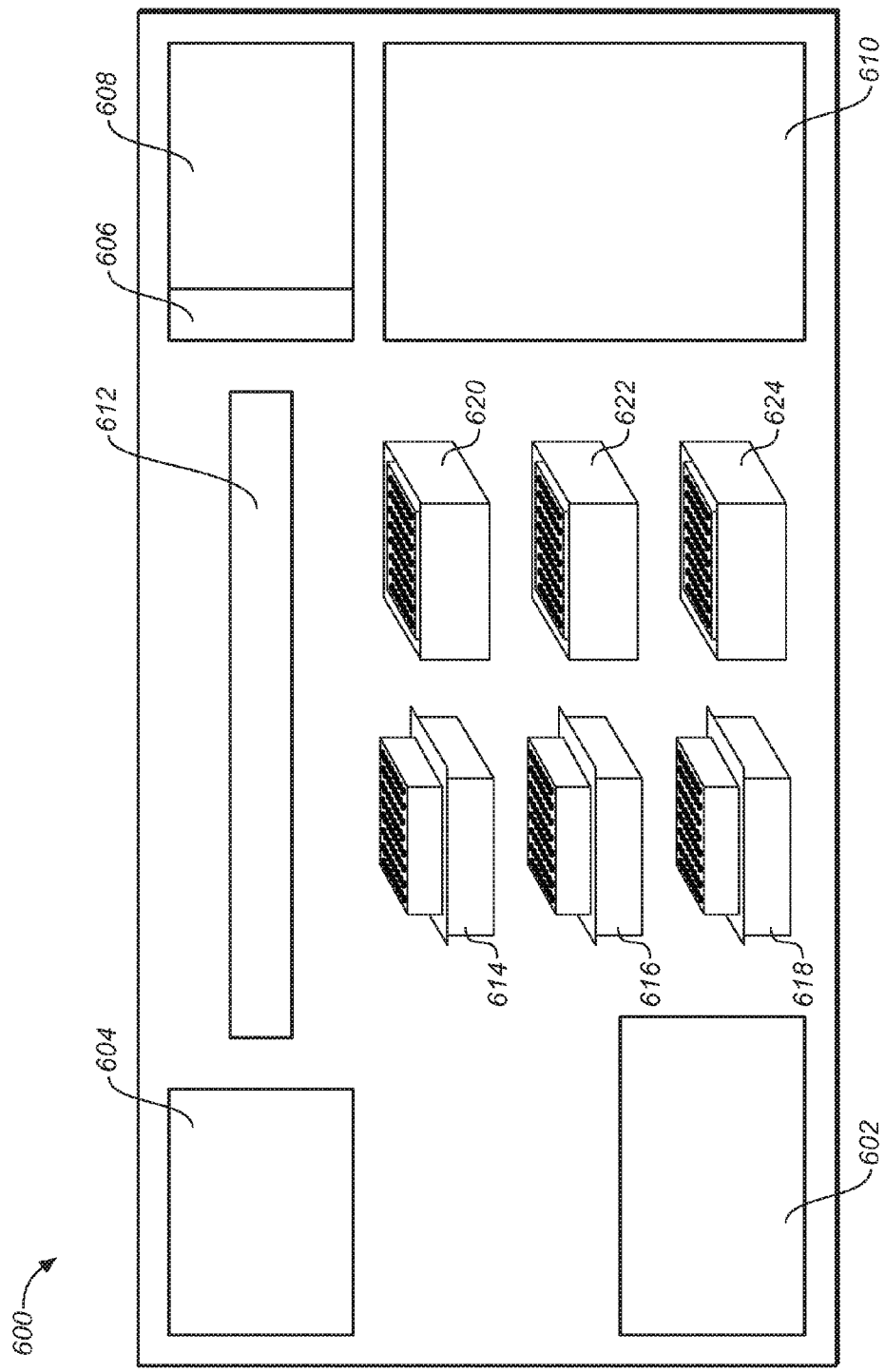
FIG. 6 illustrates one embodiment of a high-throughput sample processing system with a plurality of contactless treatment stations.

FIG. 6 illustrates one embodiment of a high-throughput sample processing system 600 with multiple contactless treatment stations. In some embodiments, the high-throughput sample processing system 600 comprises a sample dispensing device 602, a contactless fluid dispensing device 604, a contactless liquid level sensory system 606, a contactless fluid aspirator 608, a robotic arm 610, an output station 612, and a plurality of contactless treatment stations 614, 616, 618, 620, 622, and 624. In some embodiments, the plurality of contactless treatment stations may be of the same or of different types. For example, in some embodiments, contactless treatment stations 614, 616, and 618 may be a contactless mixer, such as an orbital shaker. In some embodiments, contactless treatment stations 620, 622, and 624 may be a contactless heater or incubator. In some embodiments one or more of the contactless treatment stations may be or include magnet stations for separation of magnetic beads. In some embodiments, contactless treatment stations 614, 616, 618, 620, 622, and 624 are operated in parallel, simultaneously processing multiple sample processing plates.

Figure 7:
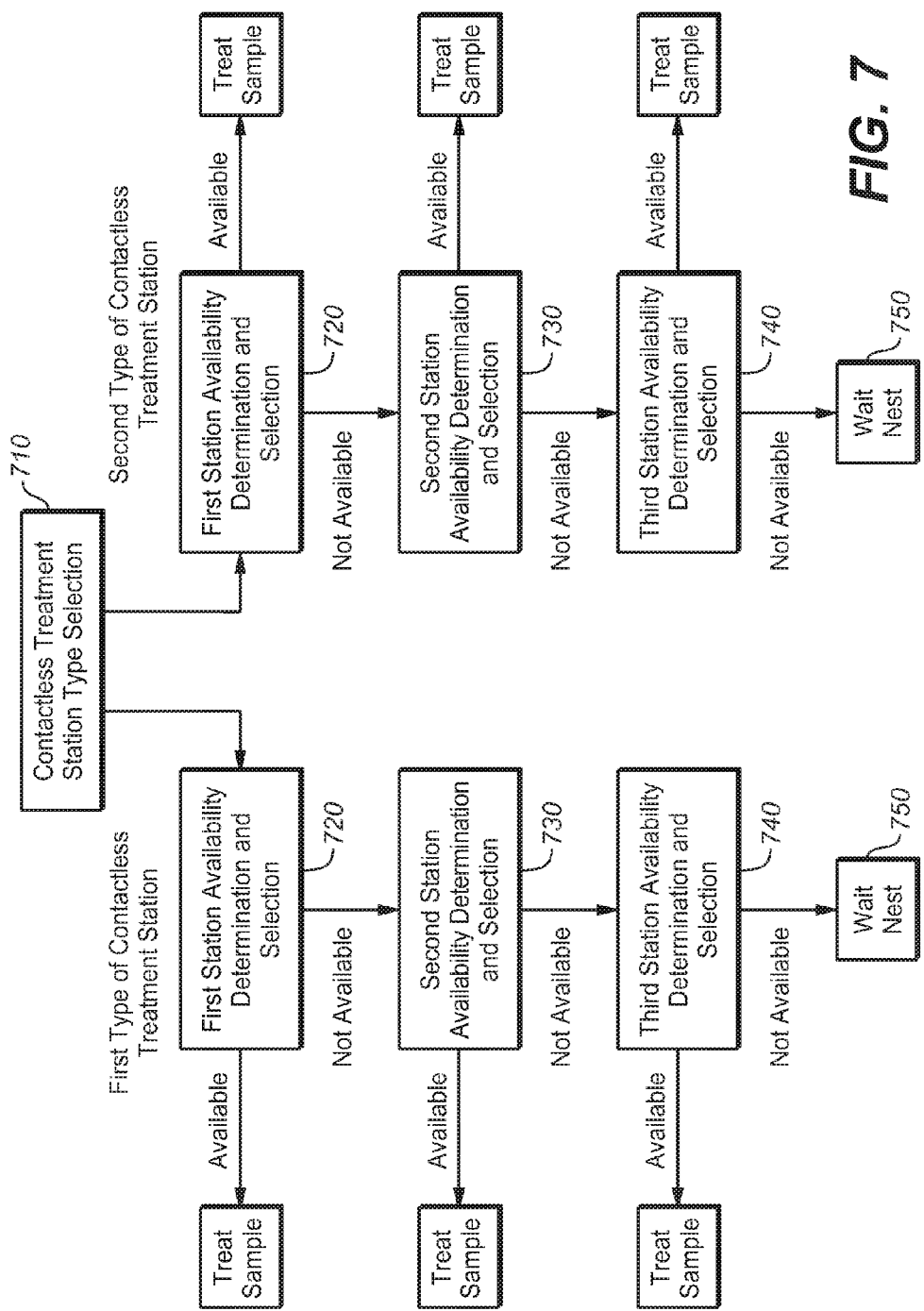
FIG. 7 is a flowchart of a method of a control system dynamically balancing parallel processing of a plurality of sample processing plates when utilizing a plurality of contactless treatment stations.

FIG. 7 is a flowchart of one embodiment of a control system dynamically selecting a contactless treatment station for a sample processing plate being processed by a high-throughput sample processing system with a plurality of different types of contactless treatment stations. At step 710, the control system determines the type of contactless treatment station is to be used to process a sample processing plate. For example, in some embodiments, the control system determines a contactless mixing station will process the sample processing plate. In some embodiments, the control system determines a contactless heating station will process the sample processing plate. In some embodiments, the control system determines a contactless cooling station will process the sample processing plate. In some embodiments, the control system determines a contactless heating-mixing station will process the sample processing plate. In some embodiments, the control system determines a contactless cooling-mixing station will process the sample processing plate.

At step 720, the control system will determine if a first contactless treatment station of the selected type is available to treat a sample processing plate. If the first contactless treatment station of the selected type is available (that is, it is not processing a different sample processing plate at the time the control system makes the determination), then the control system will activate a mechanism for transporting the sample processing plate to the first contactless treatment station of the selected type, for example by activating a robotic arm, sled, drawer, or belt. If the first contactless treatment station of the selected type is not available (that is, it is processing a different sample processing plat at the time the control system makes the determination), then, in some embodiments, the control system will proceed to step 730.

In some embodiments, at step 730, the control system will determine if a second contactless treatment station of the selected type is available to treat a sample processing plate. If the second contactless treatment station of the selected type is available, then the control system will activate a mechanism for transporting the sample processing plate to the second contactless treatment station of the selected type. If the second contactless treatment station of the selected type is not available, then, in some embodiments, the control system will proceed to step 740.

In some embodiments, at step 740, the control system will determine if a third contactless treatment station of the selected type is available to treat a sample processing plate. If the third contactless treatment station of the selected type is available, then the control system will activate a mechanism for transporting the sample processing plate to the third contactless treatment station of the selected type.

In some embodiments, if the third contactless treatment station of the selected type is not available (or no contactless treatment stations of the selected type is available), then the control system may transfer the sample processing plate to a wait nest at step 750 until a further processing station is available.

Contactless Liquid Level Sensor System

In some embodiments, a contactless liquid level sensor system comprises a one or more contactless liquid level sensors. In some embodiments, a contactless liquid level sensor can be used to determine the amount of liquid in a well of a sample processing plate. In some embodiments, an array of contactless liquid level sensors may be used in a high-throughput sample processing system to simultaneously determine the liquid level of a plurality of wells in a sample processing plate. In some embodiments, the liquid level is measured as volume of liquid within the well, approximate meniscus distance from the sensor, approximate meniscus distance from the top of the well, or approximate meniscus distance from the bottom of the well. In some embodiments, knowledge of the liquid level within a well is important for system monitoring, to ensure the contactless fluid dispensing system is dispensing the desired fluid volume and the contactless aspirating system is aspirating the desired fluid volume. This can help minimize well overflow and ensure consistency.

Figure 8:
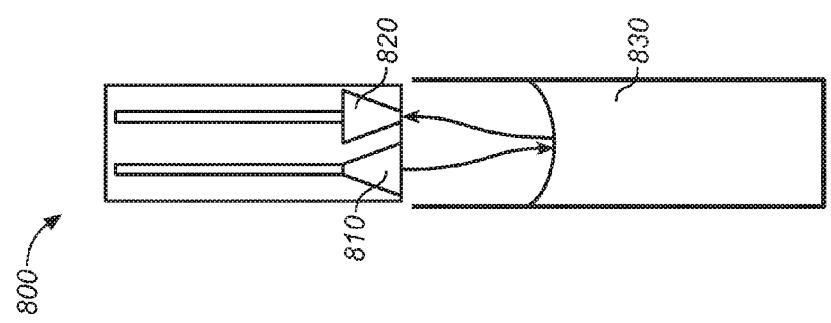
FIG. 8 illustrates an embodiment of a contactless liquid level sensor.

The liquid level can be determined in a variety of ways, for example, using weight, digital imaging, ultrasonic, or a laser level transmitter. In some embodiments, the liquid levels are measured using sonar or acoustic waves, for example ultrasonic sound waves. FIG. 8 illustrates one embodiment of a single sensor of a contactless liquid level sensor. A sensor 800 comprises a speaker 810, configured to transmit ultrasonic waves, and a microphone 820, configured to receive ultrasonic waves. The ultrasonic waves transmitted by the speaker 810 can reflect off a sample meniscus 830 and be received by the microphone 820. In some embodiments, the signals are transmitted to an amplifier. The liquid level of the sample well can be determined by the difference between the transmission and receiving time of the ultrasonic waves.

In some embodiments, the sensor has a diameter of about the same size as the diameter of the sample wells. In some embodiments, the sensor has a diameter of about 20 mm or less, about 15 mm or less, about 9 mm or less, about 7 mm or less, or about 5 mm or less, or about 2 mm or less. In some embodiments, the speaker transmits sound waves of about 20 kHz or more, about 50 kHz or more, about 150 kHz or more, about 350 kHz or more, or about 500 kHz or more. In some embodiments, the sensor has a resolution of about 50 micrometers or less, about 30 micrometers or less, about 20 micrometers or less, about 10 micrometers or less, or about 5 micrometers or less. In some embodiments, the sensor can accurately measure the distance of a meniscus less than about 5 mm away or closer, about 10 mm away or closer, about 25 mm away or closer, about 50 mm away or closer, about 100 mm away or closer, about 150 mm away or closer, or about 250 mm away or closer. In some embodiments, the liquid level can be determined in less than about 30 seconds per reading, less than about 15 seconds per reading, less than about 10 seconds per reading, less than about 5 seconds per reading, less than about 2 seconds per reading, or less than about 1 second per reading.

Contactless Fluid Aspirator

In some embodiments of a high-throughput sample processing system, a contactless fluid aspirator can be used to aspirate fluids from the plurality of wells of the sample processing plate. In some embodiments, a contactless fluid aspirator comprises one or more aspirating nozzles and a waste conduit fluidly connected to a waste management system. In some embodiments, a contactless fluid aspirator may also comprise a device for lowering aspirating nozzles, a device for raising a sample processing plate, or a magnetic base. In some embodiments, the contactless fluid aspirator may be adjoined to a contactless liquid level sensor configured to allow the determination of the liquid level of the sample wells of the sample processing plate before, during, or after the contactless fluid aspiration step.

In some embodiments, a suction force allows one or more fluid aspirating nozzles to draw fluid contained within a plurality of wells of a sample processing plate. In some embodiments, a vacuum, blower, or waste management system may provide the suction force. In some embodiments, the suction force is less than about −10 mmHg relative to ambient, less than about −15 mmHg relative to ambient, less than about −20 mmHg relative to ambient, or less than about −30 mmHg relative to ambient. In some embodiments the fluid travels through a waste management conduit to a waste management system, where it can be treated and disposed. In some embodiments, the suction force is strong enough to pull liquid from the meniscus of the sample without making contact with any retained sample. In some embodiments, the fluid aspirating nozzles are lowered into the sample wells by a device to maintain an approximately equal distance from the tip of the fluid aspirating nozzles and the meniscus of the plurality of samples. In some embodiments, the sample processing plate is raised towards stationary fluid aspirating nozzles by a device to maintain an approximately equal distance from the tip of the fluid aspirating nozzles and the meniscus of the plurality of samples.

In some embodiments, such as when magnetic affinity beads are used to bind target molecules, the sample processing plate may sit upon a magnetic base. The magnetic base forces the magnetic affinity beads to the bottom of the sample wells, thereby avoiding the suction force of the fluid aspiration nozzles. This substantially prevents sample loss during the contactless fluid aspiration step, as it decreases the likelihood affinity beads will be unintentionally aspirated from the sample wells.

In some embodiments, the contactless fluid aspirator comprise a barcode scanner, which can scan a barcode provided by the sample processing plate and transmit the location of an individual sample processing plate to a control system.

Figure 9:
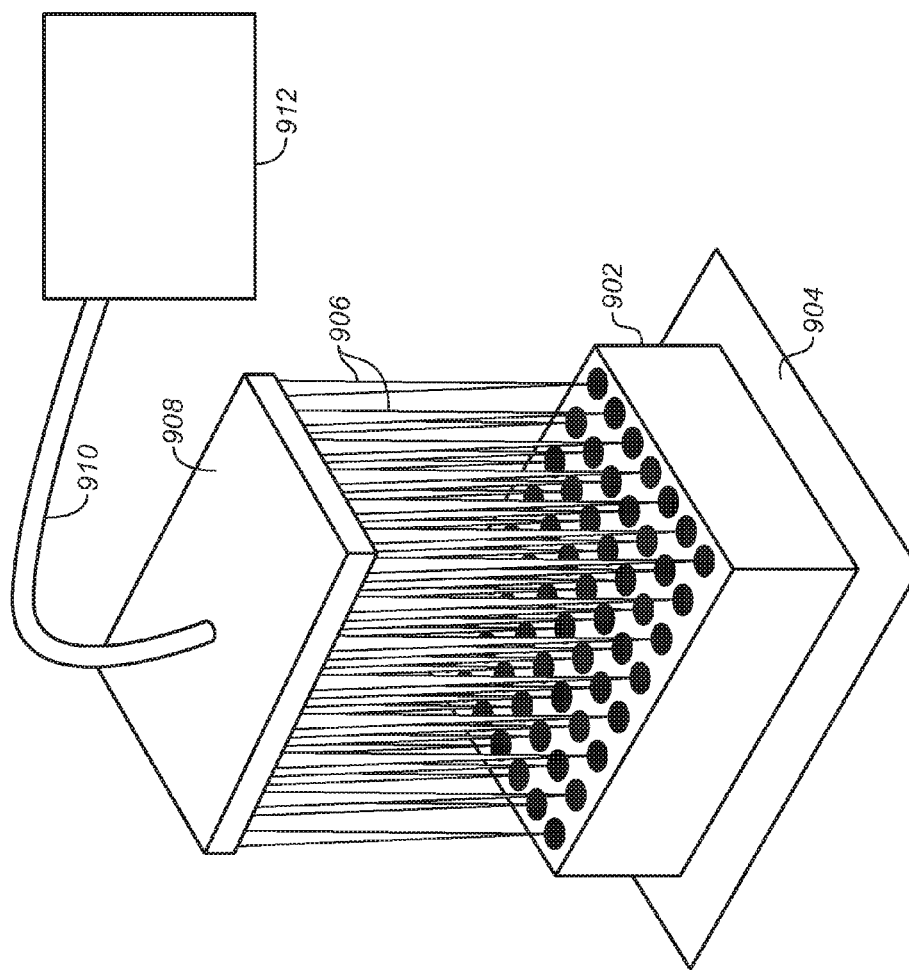
FIG. 9 illustrates an embodiment of a contactless fluid aspirator.

FIG. 9 illustrates one embodiment of a contactless fluid aspirator. The sample processing plate 902 is placed on an aspirating tray 904. In some embodiments, the aspirating tray 904 is used to transport the sample processing plate 902 between one or more components of the high-throughput sample processing system. In some embodiments, the sample processing plate 902 is placed on the aspirating tray 904 only during operation of the contactless fluid aspirator. In some embodiments, the aspirating tray 904 comprises magnets. In some embodiments, the aspirating tray 904 magnet provides a magnetic force to retain magnetic beads disposed within the plurality wells of the sample processing plate 902 during fluid aspiration. In some embodiments, this helps prevent sample loss or affinity bead loss during fluid aspiration.

In some embodiments, the contactless fluid aspirator comprises a plurality of aspirating nozzles 906. In some embodiments, the contactless fluid aspirator comprises as many aspirating nozzles 906 as there are sample wells in the sample processing plate 902. In some embodiments, the contactless fluid aspirator comprises fewer aspirating nozzles 906 than the number of sample wells in the sample processing plate 902. In some embodiments, the contactless fluid aspirator comprises as many aspirating nozzles 906 as there are wells in a single column or single row of the sample processing plate 902. In some embodiments, the aspirating nozzles are fluidly connected to a nozzle array 908.

In some embodiments, an aspirating waste conduit 910 fluidly links the nozzle array 908 with a vacuum source 912, for example a waste management system. In some embodiments, the vacuum source 912 provides a pressure gradient, allowing liquid to flow through the aspirating nozzles 906, nozzle array 908, and aspirating waste conduit 910. In some embodiments, the vacuum source 912 provides a sufficiently strong vacuum such that the aspirating nozzles 906 can siphon fluid from a sample well in the sample processing plate 902 without traversing the sample meniscus.

In some embodiments, the aspirating nozzles 906 maintain a distance from the sample meniscus such that fluid is continuously aspirated from the sample until a predetermined amount of fluid is aspirated. In some embodiments, the aspirating nozzles 906 are lowered into the sample wells of the sample processing plate 902 to maintain an appropriate distance from the sample meniscus as fluid is being aspirated. In some embodiments, the sample processing plate 902 is raised (for example by raising the aspirating tray 904) to maintain an appropriate distance between the sample meniscus and the aspirating nozzles 906 as fluid is being aspirated.

Waste Management System

In some embodiments, liquid waste from the high-throughput sample processing system is transported to a waste management system via one or more waste conduits, where it can be treated and disposed. In some embodiments, the waste conduits comprise a corrosive-resistant material, such as polytetrafluoroethylene. In some embodiments, liquid waste may be produced from washing pipette tips in the sample dispensing device, aspirated fluid from the contactless fluid aspirator, any spilled fluid during sample processing that may arise, for example overflowing of the sample processing plate wells, or fluid from priming of a pump. In some embodiments, a waste management system can treat and dispose of more than about 10 liters of liquid waste per day, more than about 20 liters of liquid waste per day, more than about 40 liters of liquid waste per day, more than about 60 liters of liquid waste per day, more than 100 liters of liquid per day, more than 200 liters of liquid per day, more than 500 liters of liquid per day, or more than 1000 liters of liquid per day.

Figure 10:
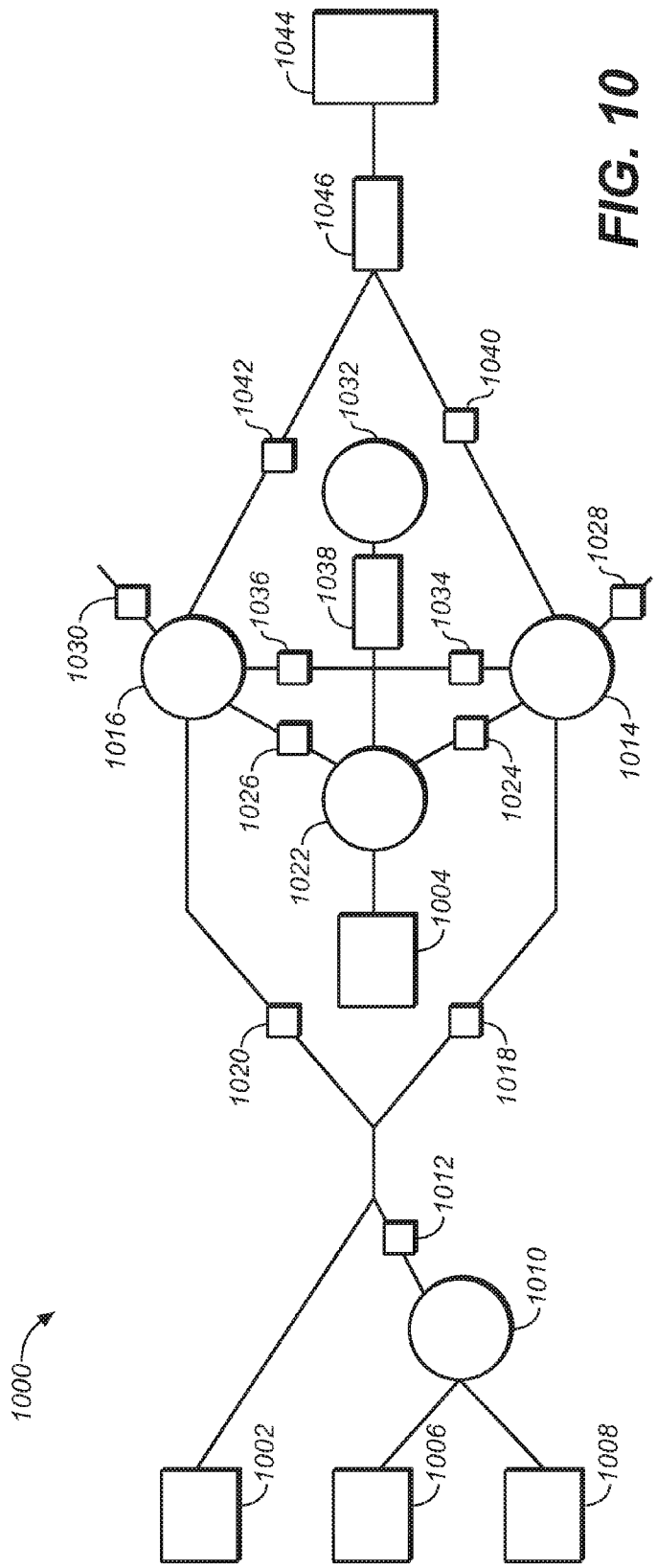
FIG. 10 illustrates a waste management system, which may be used in a high-throughput sample processing system.

FIG. 10 illustrates one embodiment of a waste management system 1000 that may be used with a high-throughput sample processing system. In some embodiments, waste may be collected by the waste management system 1000 using gravity or suction forces. In some embodiments, liquid waste from the contactless fluid aspirator 1002 flows into the waste management system 1000 using a suction force provided by suction source 1004, such as a vacuum or blower. In some embodiments, the suction source 1004 provides a pressure of less than about −10 mmHg relative to ambient, less than about −15 mmHg relative to ambient, less than about −20 mmHg relative to ambient, or less than about −30 mmHg relative to ambient. In some embodiments, liquid waste from a sample dispensing device 1006 or a waste overflow drainage tray 1008 can flow into a gravity waste collection container 1010. In some embodiments a valve 1012 can be opened by a control system to allow liquid waste to flow from the gravity waste collection container 1010 to the other components of the waste management system 1000 under suction forces. Preferably, during normal operation of the high-throughput sample processing system, valve 1012 remains closed to provide optimal suction forces for the contactless fluid aspirator 1002, opening as necessary to empty the gravity waste collection container 1010.

In some embodiments, liquid waste from the high-throughput sample processing system flows into either a first liquid waste tank 1014 or a second liquid waste tank 1016. In some embodiments, the waste management system 1000 may have more than two liquid waste tanks, while in other embodiments the waste management system 1000 may have only one liquid waste tank. A first flow valve 1018 and a second flow valve 1020 are alternatively opened (such that the first flow valve 1018 is opened when the second flow valve 1020 is closed and the first flow valve 1018 is closed when the second flow valve 1020 is opened), allowing liquid waste to flow into only one liquid waste tank at any given time. In some embodiments, the first liquid waste tank 1014 and second liquid waste tank 1016 are fluidly connected to an overflow tank 1022, which is fluidly connected to the suction source 1004. In some embodiments, a first overflow valve 1024 separates the first liquid waste tank 1014 from the overflow tank 1022 and a second overflow valve 1026 separates the second liquid waste tank 1016 from the overflow tank 1022. The first overflow valve 1024 is configured to be open when the first flow valve 1018 is opened and closed when the first flow valve 1018 is closed. Similarly, the second overflow valve 1026 is configured to be open when the second flow valve 1020 is opened and closed when the second flow valve 1020 is closed. This configuration allows the suction force generated by the suction source 1004 to pull liquid waste into the liquid waste tanks 1014 or 1016 and, in the event of overflow, into the overflow tank 1022. In some embodiments, release valves 1028 and 1030 can be disposed on the first liquid waste tank 1014 and the second liquid waste tank 1016, and can be configured to open if, for example, the liquid waste tank overflows or the pressure drops blow a predetermined pressure. The overflow tank can also be used, for example, as a vacuum ballast to maintain the vacuum in the waste system during operation. In some embodiments, the release valves 1028 and 1030 are controlled by the control system.

In some embodiments, a sterilizing solution tank 1032 comprises a sterilizing solution, for example bleach, hydrogen peroxide, or iodine solution, and is fluidly connected to the first liquid waste tank 1014 and the second liquid waste tank 1016. Once a liquid waste tank 1014 or 1016 is at a predetermined capacity, the flow valve 1018 or 1020 and the overflow valve 1026 or 1026 can be turned off and a sterilizing solution valve 1034 or 1036 can be opened. A sterilizing solution pump 1038 can pump an appropriate amount of sterilizing solution from the sterilizing solution tank 1032 into the liquid waste tank 1014 or 1016. In some embodiments the amount of sterilizing solution pumped into the liquid waste tanks 1014 or 1016 is determined by the control system after determining the weight of liquid waste in the liquid waste tanks 1014 or 1016. In some embodiments, the amount of liquid in any tank, including the liquid waste tank 1014 or 1016, the gravity waste collection container 1010, the overflow tank 1022, or the sterilizing solution tank 1032 may be determined. A variety of sensors may be used to determine the amount of fluids in the waste management system. The sensors may include, for example, acoustic sensors, weight sensors, pressure sensors etc. In some embodiments, scales can be used to determine how much fluid has flowed from the high-throughput sample processing system into the waste management system 1000. In some embodiments, the scales can determine how much fluid was aspirated from the plurality of wells in a sample processing plate by the contactless fluid aspirator that flowed to a liquid waste container 1014 or 1016. Scales are useful for determining the amount of fluids removed under vacuum. In some embodiments, the amount of fluid traveling through the system is monitored, for example, to determine whether there is a leak or error in the system. Scales and/or other sensors may be used for wastes and liquids in the waste management system that are not under valcuum, e.g., acoustic, pressure.

A series of valves may be included to ensure the proper operation of vacuum. In some embodiments the waste is removed using gravity. In some embodiments, the waste management system mixes the fluids removed from the plurality of wells with bleach in the waste container and incubates the mixture. In some embodiments, the waste management system comprises one or more sensors for determining an amount of fluids removed from the plurality of wells. These sensors may include, for example, acoustic sensors, weight sensors, pressure sensors etc. In some embodiments, the waste management system comprises one or more scales for determining an amount of fluids removed from the plurality of wells using a vacuum.

In some embodiments, after the sterilizing solution has been injected into the liquid waste tank 1014 or 1016, the liquid waste is incubated for a predetermined period of time, allowing the neutralization of any biohazardous material. In some embodiments, the liquid waste incubates for 5 minutes or more, 15 minutes or more, 30 minutes or more, 60 minutes or more, or 120 minutes or more, or 180 minutes or more. After incubation of the liquid waste, a drainage valve 1040 or 1042 is opened, allowing the waste to drain from the waste management system 1000 into an appropriate location, for example a holding tank or sewage system 1044. In some embodiments, release valves 1028 or 1030 may be opened or drainage pump 1046 can pump liquid from the liquid waste tanks 1014 or 1016 to accelerate expulsion of the liquid. In some embodiments, the treated liquid waste is disposed of in sewage pipes.

In some embodiments, a control system monitors volumes of the liquid waste tank 1014 or 1016, the gravity waste collection container 1010, the overflow tank 1022, or the sterilizing solution tank 1032. In some embodiments, a control system monitors flow levels of the sterilizing solution pump 1038 or the drainage pump 1046. In some embodiments, the control system monitors pressures within the waste management system 1000. In some embodiments, if any volume, pump flow level, or pressure is above a predetermined value or below a predetermined value, the control system may signal an alarm or terminate the high-throughput sample processing system operation.

By including a waste management system, a high-throughput sample processing system can continuously process and dispose of liquid waste resulting from system use. The waste management system increases worker safety, as there is decreased likelihood of contact with the liquid waste. Furthermore, allowing the waste to be continuously treated and disposed of decreases the expense of liquid waste collection and off-site disposal, providing a more cost-effective system than previously known sample treatment methods and to allow for unattended operation of the system.

Exemplary Embodiments

The invention is further described by the following embodiments.

Embodiment 1. In one embodiment a high throughput sample processing system comprises: a sample dispensing device for drawing a plurality of samples from a plurality of sample containers and for dispensing each sample into a well of a sample processing plate comprising a plurality of wells, wherein each sample is dispensed into a different well; a fluid dispensing device for dispensing fluids into the plurality of wells of the sample processing plate; a plurality of liquid level sensors for detecting the liquid level in each of the plurality of wells of the sample processing plate; a plurality of aspirators for removing fluids from the plurality of wells of the sample processing plate; a plurality of treatment stations for treating a plurality of sample processing plates simultaneously; a waste management system for managing fluids removed from the plurality of wells; and a control system for controlling the processing of a plurality of plates within the high throughput sample processing system simultaneously.

Embodiment 2. In a further embodiment of embodiment 1 or any exemplarily embodiment herein, the control system dynamically controls the processing of a plate depending upon the location or status of other plates in the system.

Embodiment 3. In a further embodiment of embodiment 1, 2 or any exemplarily embodiment herein, the high throughput sample processing system comprises one or more magnetic stations.

Embodiment 4. In a further embodiment of embodiment 1-3 or any exemplarily embodiment herein, the fluid dispensing device is contactless.

Embodiment 5. In a further embodiment of embodiment 1-4 or any exemplarily embodiment herein, the liquid level sensors are contactless.

Embodiment 6. In a further embodiment of embodiment 1-5 or any exemplarily embodiment herein, the treatment stations are contactless.

Embodiment 7. In a further embodiment of embodiment 1-6 or any exemplarily embodiment herein, the high throughput sample comprises a plate loading device for automatically loading additional plates into the sample dispensing device.

Embodiment 8. In a further embodiment of embodiment 1-7 or any exemplarily embodiment herein, the samples comprise blood, saliva, and/or plasma.

Embodiment 9. In a further embodiment of embodiment 1-8 or any exemplarily embodiment herein, the high throughput system extracts DNA from the plurality of samples using magnetic beads.

Embodiment 10. In a further embodiment of embodiment 1-9 or any exemplarily embodiment herein, the sample dispensing device comprises a plurality of syringe based pipettes.

Embodiment 11. In a further embodiment of embodiment 1-10 or any exemplarily embodiment herein, the sample dispensing device comprises a plurality of reusable syringe based pipettes.

Embodiment 12. In a further embodiment of embodiment 10, 11 or any exemplarily embodiment herein, the sample dispensing device comprises a washing station for automatically washing the reusable pipette tips.

Embodiment 13. In a further embodiment of embodiment 12 or any exemplarily embodiment herein, the washing station comprises a bleach solution.

Embodiment 14. In a further embodiment of embodiment 1-13 or any exemplarily embodiment herein, the sample containers are sealed and pipettes are configured to draw the plurality of samples through seals of the containers.

Embodiment 15. In a further embodiment of embodiment 1-14 or any exemplarily embodiment herein, the liquid level sensors comprise one or more acoustic sensors.

Embodiment 16. In a further embodiment of embodiment 1-15 or any exemplarily embodiment herein, the waste management system deposits the fluids removed from the plurality of wells into a waste container.

Embodiment 17. In a further embodiment of embodiment 16 or any exemplarily embodiment herein, the waste container operates under a vacuum.

Embodiment 18. In a further embodiment of embodiment 1-17 or any exemplarily embodiment herein, the waste management system mixes the fluids removed from the plurality of wells with bleach in the waste container and incubates the mixture.

Embodiment 19. In a further embodiment of embodiment 1-18 or any exemplarily embodiment herein, the waste management system comprises one or more scales for determining an amount of fluids removed from the plurality of wells.

Embodiment 20. In a further embodiment of embodiment 1-19 or any exemplarily embodiment herein, the plurality of treatment stations comprise one or more mixing devices.

Embodiment 21. In a further embodiment of embodiment 20 or any exemplarily embodiment herein, the one or more mixing devices comprises one or more orbital shakers.

Embodiment 22. In a further embodiment of embodiment 1-21 or any exemplarily embodiment herein, the plurality of treatment stations comprise one or more heating or cooling devices.

Embodiment 23. In a further embodiment of embodiment 1-22 or any exemplarily embodiment herein, the high throughput sample processing system comprises a barcode scanner for identifying samples using barcodes on the sample containers.

Embodiment 24. In one embodiment a high throughput sample processing method comprises: drawing a plurality of samples from a plurality of sample containers; dispensing each sample into a well of a sample processing plate comprising a plurality of wells, wherein each sample is dispensed into a different well; dispensing fluids into the plurality of wells of the sample processing plate using a contactless fluid dispensing device; detecting the liquid level in each of the plurality of wells of the sample processing plate using a plurality of contactless liquid level sensors; mixing a plurality of sample processing plates simultaneously using a plurality of contactless mixing devices; removing fluids from the plurality of wells of the sample processing plate using a plurality of aspirators; and managing fluids removed from the plurality of wells using a waste management system.

Embodiment 25. In a further embodiment of embodiment 24 or any exemplarily embodiment herein, comprising dynamically controlling the processing of a plate depending upon the location or status of other plates.

Embodiment 26. In a further embodiment of embodiment 24, 25, or any exemplarily embodiment herein, further comprising automatically loading additional plates into the sample dispensing device.

Embodiment 27. In a further embodiment of embodiment 24-26 or any exemplarily embodiment herein, the plurality of samples comprise blood, plasma or saliva.

Embodiment 28. In a further embodiment of embodiment 24-27 or any exemplarily embodiment herein, the method comprises extraction of DNA from the plurality of samples using magnetic beads.

Embodiment 29. In a further embodiment of embodiment 24-28 or any exemplarily embodiment herein, the samples are dispensed using a plurality of syringe based pipettes.

Embodiment 30. In a further embodiment of embodiment 29 or any exemplarily embodiment herein, the pipettes comprise reusable pipette tips.

Embodiment 31. In a further embodiment of embodiment 29-30 or any exemplarily embodiment herein, further comprising automatically washing the reusable pipette tips.

Embodiment 32. In a further embodiment of embodiment 29-31 or any exemplarily embodiment herein, the pipette tips are automatically washed using a bleach solution.

Embodiment 33. In a further embodiment of embodiment 24-31 or any exemplarily embodiment herein, the liquid level sensors comprise one or more acoustic sensors.

Embodiment 34. In a further embodiment of embodiment 24-33 or any exemplarily embodiment herein, the waste management system deposits the fluids removed from the plurality of wells into a waste container.

Embodiment 35. In a further embodiment of embodiment 24-34 or any exemplarily embodiment herein, the waste container operates under a vacuum.

Embodiment 36. In a further embodiment of embodiment 24-35 or any exemplarily embodiment herein, the waste management system mixes the fluids removed from the plurality of wells with bleach in the waste container and incubates the mixture.

Embodiment 37. In a further embodiment of embodiment 24-36 or any exemplarily embodiment herein, the waste management system comprises one or more scales for determining an amount of fluids removed from the plurality of wells.

Embodiment 38. In a further embodiment of embodiment 24-37 or any exemplarily embodiment herein, the plurality of contactless mixing devices comprises one or more orbital shakers.

Embodiment 39. In a further embodiment of embodiment 24-38 or any exemplarily embodiment herein, comprising scanning a barcode scanner on the sample containers to identify the samples.

Embodiment 40. An embodiment of a non-transitory computer-readable storage medium for operating a high throughput sample processing system, the computer-readable storage medium comprising instructions for: dynamically scheduling multiple sample processing plates for processing through a sample processing system, wherein the scheduling depends upon the location or status of other sample processing plates in the sample processing system; controlling one or more robotic mechanisms for transferring sample processing plates among devices within the sample processing system according to the dynamic scheduling; operating a sample dispensing device operable for drawing a plurality of samples from a plurality of sample containers and for dispensing each sample into a well of a sample processing plate comprising a plurality of wells, wherein each sample is dispensed into a different well; operating a contactless fluid dispensing device operable for dispensing fluids into the plurality of wells of each of the sample processing plates; operating a plurality of contactless liquid level sensors operable for detecting the liquid level in each of the plurality of wells of each of the sample processing plates; operating a plurality of aspirators for removing fluids from the plurality of wells of each of the sample processing plates; operating a plurality of contactless mixing devices for mixing a plurality of sample processing plates simultaneously; and operating a waste management system for managing fluids removed from the plurality of wells.

Embodiment 41. In a further embodiment of embodiment 40 or any exemplarily embodiment herein, the plurality of samples comprise blood, plasma or saliva.

Embodiment 42. In a further embodiment of embodiment 40-41 or any exemplarily embodiment herein, wherein the instructions comprises instructions for extraction of DNA from the plurality of samples using magnetic beads.

Embodiment 43. In a further embodiment of embodiment 40-42 or any exemplarily embodiment herein, the samples are dispensed using a plurality of syringe based pipettes.

Embodiment 44. In a further embodiment of embodiment 43 or any exemplarily embodiment herein, the pipettes comprise reusable pipette tips.

Embodiment 45. In a further embodiment of embodiment 43-44 or any exemplarily embodiment herein, further comprising automatically washing the reusable pipette tips.

Embodiment 46. In a further embodiment of embodiment 43-45 or any exemplarily embodiment herein, the pipette tips are automatically washed using a bleach solution.

Embodiment 47. In a further embodiment of embodiment 24-31 or any exemplarily embodiment herein, the liquid level sensors comprise one or more acoustic sensors.

Embodiment 48. In a further embodiment of embodiment 40-47 or any exemplarily embodiment herein, the waste management system deposits the fluids removed from the plurality of wells into a waste container.

Embodiment 49. In a further embodiment of embodiment 40-48 or any exemplarily embodiment herein, the waste container operates under a vacuum.

Embodiment 50. In a further embodiment of embodiment 40-49 or any exemplarily embodiment herein, the waste management system mixes the fluids removed from the plurality of wells with bleach in the waste container and incubates the mixture.

Embodiment 51. In a further embodiment of embodiment 40-50 or any exemplarily embodiment herein, the waste management system comprises one or more scales for determining an amount of fluids removed from the plurality of wells.

Embodiment 52. In a further embodiment of embodiment 40-51 or any exemplarily embodiment herein, the plurality of contactless mixing devices comprises one or more orbital shakers.

Embodiment 53. In a further embodiment of embodiment 40-52 or any exemplarily embodiment herein, wherein the instructions comprises instructions for scanning a barcode scanner on the sample containers to identify the samples.

Embodiment 54. An embodiment of a waste management system for processing waste produced by a high-throughput sample processing system, comprises: a gravity-based liquid waste input; a vacuum-based liquid waste input; a sterilizing fluid container; two or more liquid waste containers, configured to alternatively accept liquid waste, treat the liquid waste with a sterilizing fluid, and incubate the sterilizing fluid in the liquid waste for a predetermined period of time before disposing of the treated liquid waste; and one or more scales for determining the amount of liquid waste collected by the one or more liquid waste containers.

Embodiment 55. In a further embodiment of embodiment 54 or any exemplarily embodiment herein, the sterilization fluid comprises bleach.

This application discloses several numerical ranges in the text and figures. The numerical ranges disclosed inherently support any range or value within the disclosed numerical ranges even though a precise range limitation is not stated verbatim in the specification because this invention can be practiced throughout the disclosed numerical ranges.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. Finally, the entire disclosure of the patents and publications referred in this application are hereby incorporated herein by reference.

What is claimed is:
1. A high throughput sample processing method comprising:
 drawing a plurality of samples from a plurality of sample containers using a sample dispensing device;
 dispensing each sample using the sample dispensing device, wherein each sample is dispensed into a well of a sample processing plate comprising a plurality of wells, wherein each sample is dispensed into a different well;

dispensing fluids into the plurality of wells of the sample processing plate using a contactless fluid dispensing device;

detecting the liquid level in each of the plurality of wells of the sample processing plate using a plurality of contactless liquid level sensors;

mixing a plurality of sample processing plates simultaneously using a plurality of contactless mixing devices;

removing fluids from the plurality of wells of the sample processing plate using a plurality of aspirators; and managing fluids removed from the plurality of wells using a waste management system;

wherein the steps of the high throughput sample processing method are scheduled and coordinated by a control system.

2. The method of claim 1, comprising dynamically controlling the processing of a plate depending upon the location or status of other plates using the control system.

3. The method of claim 1, further comprising automatically loading additional plates into the sample dispensing device using a plate loading device.

4. The method of claim 1, wherein the plurality of samples comprise blood, plasma or saliva.

5. The method of claim 1, wherein the method comprises extraction of DNA from the plurality of samples using magnetic beads disposed within the plurality of wells of the sample processing plate.

6. The method of claim 1, wherein the samples are dispensed using a plurality of syringe based pipettes.

7. The method of claim 1, wherein the liquid level sensors comprise one or more acoustic sensors.

8. The method of claim 1, wherein the waste management system is configured to deposit the fluids removed from the plurality of wells into a waste container.

9. The method of claim 1, wherein the waste management system is configured to mix the fluids removed from the plurality of wells with bleach in the waste container and incubate the mixture.

10. The method of claim 1, wherein the waste management system comprises one or more scales for determining an amount of fluids removed from the plurality of wells.

11. The method of claim 1, wherein the plurality of contactless mixing devices comprises one or more orbital shakers.

12. The method of claim 1, comprising scanning a barcode on the sample containers to identify the samples.

* * * * *